(12) United States Patent
Frisken et al.

(10) Patent No.: US 12,133,686 B2
(45) Date of Patent: Nov. 5, 2024

(54) APPARATUS AND METHOD FOR IN-VIVO MEASUREMENT OF CORNEAL BIOMECHANICAL RESPONSE

(71) Applicant: Cylite Pty Ltd, Notting Hill (AU)

(72) Inventors: Steven James Frisken, Vaucluse (AU); Grant Andrew Frisken, Mitcham (AU); Trevor Bruce Anderson, Notting Hill (AU)

(73) Assignee: Cylite Pty Ltd, Notting Hill (AU)

( * ) Notice: Subject to any disclaimer, the term of this patent is extended or adjusted under 35 U.S.C. 154(b) by 938 days.

(21) Appl. No.: 16/972,578

(22) PCT Filed: Jun. 4, 2019

(86) PCT No.: PCT/AU2019/050571
§ 371 (c)(1),
(2) Date: Dec. 5, 2020

(87) PCT Pub. No.: WO2019/232575
PCT Pub. Date: Dec. 12, 2019

(65) Prior Publication Data
US 2021/0244278 A1 Aug. 12, 2021

(30) Foreign Application Priority Data
Jun. 5, 2018 (AU) ............................. 2018902018

(51) Int. Cl.
*A61B 3/16* (2006.01)
*A61B 3/00* (2006.01)
(Continued)

(52) U.S. Cl.
CPC .............. *A61B 3/16* (2013.01); *A61B 3/0008* (2013.01); *A61B 3/0025* (2013.01); *A61B 3/101* (2013.01); *A61B 3/107* (2013.01)

(58) Field of Classification Search
CPC ........ A61B 3/16; A61B 3/0008; A61B 3/0025; A61B 3/101; A61B 3/107; A61B 3/1005; A61B 3/102; A61B 3/165
(Continued)

(56) References Cited

U.S. PATENT DOCUMENTS

| 4,747,683 A | 5/1988 | Doane |
| 5,148,807 A * | 9/1992 | Hsu .................... A61B 3/165 |
| | | 600/402 |

(Continued)

FOREIGN PATENT DOCUMENTS

| CN | 103491855 A | 1/2014 |
| CN | 105530853 A | 4/2016 |
| WO | 2012/110051 | 8/2012 |
| WO | 2018/136993 | 8/2018 |

OTHER PUBLICATIONS

Scarcelli et al 'Biomechanical characterization of keratoconus corneas ex vivo with Brillouin microscopy', Investigative Ophthalmology & Visual Science 55(7), 4490-4495 (2014).
(Continued)

*Primary Examiner* — Tuyen Tra
*Assistant Examiner* — Rahman Abdur
(74) *Attorney, Agent, or Firm* — MATTINGLY & MALUR, PC

(57) ABSTRACT

Apparatus and methods are presented for non-contact in-vivo measurement of one or more properties of a cornea or tear film with spatial resolution. In certain embodiments the cornea/tear film is probed at substantially normal incidence with a converging array of beamlets from a multi-wavelength optical source, and the reflected light analysed interferometrically to generate a time sequence of pachymetry maps. Thickness variations arising from differences between the external and intraocular pressure, e.g. from the ocular pulse or externally applied pressure changes, are measured
(Continued)

and analysed to obtain information on a biomechanical response of the cornea. In preferred embodiments the time variation in tear film thickness is measured and subtracted to yield normalised pachymetry data for the biomechanical analysis. In certain embodiments the apparatus is configured to measure the dynamics and profile of the tear film, using either converging or substantially parallel arrays of beamlets.

28 Claims, 10 Drawing Sheets

(51) Int. Cl.
*A61B 3/10* (2006.01)
*A61B 3/107* (2006.01)

(58) Field of Classification Search
USPC .......................................................... 351/212
See application file for complete search history.

(56) References Cited

U.S. PATENT DOCUMENTS

| | | | |
|---|---|---|---|
| 5,317,389 A | 5/1994 | Hochberg | |
| 5,861,955 A | 1/1999 | Gordon | |
| 6,454,761 B1 | 9/2002 | Freedman | |
| 7,800,759 B2 | 9/2010 | Lai et al. | |
| 9,668,647 B2 | 6/2017 | Grenon et al. | |
| 2005/0197571 A1* | 9/2005 | McVeigh | A61B 8/13 600/437 |
| 2006/0066869 A1 | 3/2006 | Ueno et al. | |
| 2007/0121067 A1* | 5/2007 | Davis | A61B 3/16 351/212 |
| 2011/0273669 A1 | 11/2011 | Abitbol et al. | |
| 2011/0285961 A1 | 11/2011 | Korb | |
| 2013/0321822 A1 | 12/2013 | Vogler et al. | |
| 2014/0118699 A1 | 5/2014 | Huth | |
| 2014/0148658 A1* | 5/2014 | Zalevsky | A61B 5/0816 600/301 |
| 2014/0323862 A1 | 10/2014 | Silverman | |
| 2015/0018661 A1 | 1/2015 | Yen | |
| 2015/0032090 A1 | 1/2015 | Gonzalez | |
| 2015/0313573 A1 | 11/2015 | Liu | |
| 2016/0174834 A1 | 6/2016 | Eslami | |
| 2016/0220110 A1 | 8/2016 | Vogler | |
| 2016/0345820 A1 | 12/2016 | Frisken | |
| 2017/0189233 A1 | 7/2017 | Dewey | |
| 2017/0290503 A1 | 10/2017 | Larin | |
| 2017/0332897 A1 | 11/2017 | Arieli | |
| 2018/0146851 A1 | 5/2018 | Frisken | |

OTHER PUBLICATIONS

McAlinden et al 'A comprehensive evaluation of the precision (repeatability and reproducibility) of the Oculus Pentacam HR', Investigative Ophthalmology & Visual Science 52(10), 7731-7737 (2011).
Correa-Pérez et al 'Precision of high definition spectral-domain optical coherence tomography for measuring central corneal thickness', Investigative Ophthalmology & Visual Science 53(4), 1752-1757 (2012).
King-Smith et al 'Mechanisms, imaging and structure of tear film breakup', The Ocular Surface 16, 4-30 (2018).
Dos Santos et al 'In vivo tear film thickness measurement and tear film dynamics visualization using spectral domain optical coherence tomography', Optics Express 23(16), 21043-21063 (2015).
King-Smith et al 'Tear film interferometry and corneal surface roughness', Investigative Ophthalmology & Visual Science 55(4), 2614-2618 (2014).
Manapuram et al 'In vivo estimation of elastic wave parameters using phase-stabilized swept source optical coherence elastography', Journal of Biomedical Optics 17(10), 100501 (2012).
Ford et al 'Method for optical coherence elastography of the cornea', Journal of Biomedical Optics 16(1), 016005 (2011).
Wang et al 'Shear wave imaging optical coherence tomography (SWI-OCT) for ocular tissue biomechanics', Optics Letters 39(1), 41-44 (2014).
Lepert et al 'Assessing corneal biomechanics with Brillouin spectro-microscopy', Faraday Discussions 187, 415-428 (2016).
Scarcelli et al 'Brillouin optical microscopy for corneal biomechanics', Investigative Ophthalmology & Visual Science 53(1), 185-190 (2012).
Oliveira et al 'Corneal imaging with slit-scanning and Scheimpflug imaging techniques', Clinical and Experimental Optometry 94(1), 33-42 (2010).
Punjabi et al 'Dynamic contour tonometry: principle and use', Clinical and Experimental Ophthalmology 34, 837-840 (2006).
Werkmeister et al 'Measurement of tear film thickness using ultrahigh-resolution optical coherence tomography', Investigate Ophthalmology & Visual Science 54(8), 5578-5583 (2013).
Yadav et al 'Micrometer axial resolution OCT for corneal imaging', Biomedical Optics Express 2(11), 3037-3046 (2011).
Gumus et al 'Anterior segment optical coherence tomography (AS-OCT) in the management of dry eye', International Ophthalmology Clinics 57(2), 13-22 (2017).
Lu et al 'Tear film measurement by optical reflectometry technique', Journal of Biomedical Optics 19(2), 027001 (2014).
Clayson et al 'Corneal deformation before and after corneal crosslinking (CXL) in response to ocular pulse' Investigative Ophthalmology & Visual Science 59, 1391 (2018) [This is the published abstract of a poster presented at the ARVO 2018 conference, held in Honolulu from Apr. 29 to May 3, 2018, abstract was published in Jul. 2018 (after claimed priority date).
Photograph of part of the actual Clayson et al poster.
Greenwald et al, 'Corneal imaging; An Introduction' Opthamology and Visual Sciences, Oct. 19, 2016.
Extended European Search Report received in corresponding European Application No. 19814657.3 dated Jul. 12, 2021.
Chinese Office Action received in corresponding Chinese Application No. 201980037163.8 dated Jan. 11, 2024.
Australian Office Action received in corresponding Australian Application No. 2019280447 dated Feb. 7, 2024.

\* cited by examiner

APPARATUS AND METHOD FOR IN-VIVO MEASUREMENT OF CORNEAL BIOMECHANICAL RESPONSE

FIELD OF THE INVENTION

The invention relates to apparatus and methods for optical metrology, in particular for in-vivo measurement of the biomechanical response of the human cornea. However it will be appreciated that the invention is not limited to this particular field of use.

RELATED APPLICATIONS

The present application claims priority from Australian Provisional Patent Application No 2018902018 filed on 5 Jun. 2018, the contents of which are incorporated herein by reference.

BACKGROUND OF THE INVENTION

Any discussion of the prior art throughout the specification should in no way be considered as an admission that such prior art is widely known or forms part of the common general knowledge in the field.

Keratoconus is a degenerative condition in which localised thinning and reduced rigidity leads to distortion of the cornea, directly impairing the quality of vision. While the corneal distortions characteristic of more advanced keratoconus are easily detectable by corneal topography or pachymetry, it is preferable to be able to detect the condition at an earlier stage. This would allow for example the screening of people at risk of developing keratoconus so that strategies for managing the condition can be put in place before permanent damage occurs, as well as patient screening prior to refractive surgery. It is thought that early detection of keratoconus, among other corneal diseases, can be effectively achieved by measuring the biomechanical properties of the eye, looking for localised weakening of the cornea. In particular, the focal region of the keratoconic cone is weakened and has different biomechanical properties from other regions of the cornea. This approach may provide discrimination from other perturbations of the cornea that could complicate a diagnosis based purely on geometric features such as corneal elevation and thickness maps.

One technique for measuring the mechanical response of human tissue such as the cornea is optical coherence elastography (OCE), described for example in published US patent application No 2017/0290503 A1 entitled 'Optical coherence elastography to assess biomechanics and detect progression of ocular and other tissues degenerative diseases'. Vibrations in the tissue are excited, e.g. by air puff, ultrasound or mechanical contact, and the mechanical response measured by optical coherence tomography (OCT). A difficulty with using OCE for corneal measurements is the need to separate the effect of intraocular pressure (IOP) variations from abnormalities in the cornea.

Brillouin microscopy has been proposed as a technique for mapping the mechanical strength across a cornea, at least ex-vivo. As described for example in Scarcelli et al 'Biomechanical characterization of keratoconus corneas ex vivo with Brillouin microscopy', *Investigative Ophthalmology & Visual Science* 55(7), 4490 (2014), Brillouin shift measurements can provide information on the longitudinal modulus of the cornea. However the apparatus is relatively expensive because of the need for a high-resolution spectrometer. Furthermore the technique is time consuming because of the scanning requirement and requires a high on-eye optical intensity, presenting a challenge for in-vivo use.

Several types of pachymeter for measuring corneal thickness are known, based for example on ultrasonic techniques such as corneal waveform or optical techniques such as OCT, slit-scanning and Scheimpflug imaging. However these techniques may not have sufficient precision for measuring small spatial or temporal variations in thickness associated with a biomechanical response of the cornea, with repeatability of around ±5 μm being reported for many commercially available instruments, see for example McAlinden et al 'A comprehensive evaluation of the precision (repeatability and reproducibility) of the Oculus Pentacam HR', *Investigative Ophthalmology & Visual Science* 52(10), 7731 (2011) and Correa-Perez et al 'Precision of high definition spectral-domain optical coherence tomography for measuring central corneal thickness', *Investigative Ophthalmology & Visual Science* 53(4), 1752 (2012). Optical reflectometry techniques for measuring tear film thickness have much higher precision, of order of several nm, but are not well suited for measuring corneal thickness which is some two orders of magnitude greater than tear film thickness, especially when measuring over a large area of the cornea.

Studies of the pressure induced-deformation of the cornea have shown that the eye and cornea experience a creep in shape due to variations of IOP of approximately ±3 to 6 mm Hg associated with a number of factors including heart rate, posture change, fluid intake, diurnal cycle and certain drugs. These shape changes are measurable with conventional topographical techniques such as Placido disc topography over periods of many seconds or longer. It is also known that IOP fluctuates with ocular pulse, as reported in published US patent application No 2015/0313573 A1 entitled 'Ophthalmic elastography', using a contacting ultrasound technique applied ex-vivo with a simulated pulse. However these pulse-related shape changes are generally about an order of magnitude smaller than those caused by the more gradual IOP variations mentioned previously, and it is difficult to measure corneal thickness non-invasively and in-vivo with the level of sensitivity required to assess the underlying biomechanics of the cornea.

The corneal tear film plays an important role in eye health, as well as in vision since it is the first refractive surface encountered by light rays entering the eye, with abnormal tear film breakup implicated in dry eye disease and vision aberrations. As reviewed recently in King-Smith et al 'Mechanisms, imaging and structure of tear film breakup', *The Ocular Surface* 16, 4 (2018), the dynamics and causes of tear film breakup have been studied over many years. Tear film thickness and surface shape are both important for determining tear film dynamics, but current imaging techniques are limited to measuring either thickness or surface shape. Spectral domain OCT has been used to measure tear film thickness, see for example dos Santos et al 'In vivo tear film thickness measurement and tear film dynamics visualization using spectral domain optical coherence tomography', *Optics Express* 23(16), 21043 (2015), but has not provided information on surface shape. There is a need then for an apparatus that can measure tear film thickness and dynamics over an extended region wherein the shape and position of the eye can be taken into account.

Unless the context clearly requires otherwise, throughout the description and the claims the words 'comprising', 'comprises' and the like are to be construed in an inclusive sense as opposed to an exclusive or exhaustive sense. That is, they are to be construed in the sense of 'including, but not limited to'.

OBJECT OF THE INVENTION

It is an object of the present invention to overcome or ameliorate at least one of the limitations of the prior art, or to provide a useful alternative. It is an object of the present invention in a preferred form to provide an apparatus for snapshot in-vivo measurement of one or more corneal properties at multiple points across the cornea. It is another object of the present invention in a preferred form to provide an apparatus for in-vivo measurement of time variations in corneal thickness or strain. It is another object of the present invention in a preferred form to provide a method for measuring tear film dynamics over an extended region of the cornea.

SUMMARY OF THE INVENTION

According to a first aspect of the present invention there is provided an apparatus for measuring one or more properties of a cornea, said apparatus comprising:
a first optical system comprising an optical source and a spatial sampling element for generating a converging array of beamlets configured to impinge simultaneously on at least a portion of a front surface of a cornea; and
a second optical system for:
capturing reflected or scattered light from said front surface and reflected or scattered light from a second surface or interface of said cornea;
measuring relative phase between the reflected or scattered light from said front surface and the reflected or scattered light from said second surface or interface across the portion of said cornea illuminated by said beamlets; and
monitoring said relative phase over time to obtain information on one or more properties of said cornea across the illuminated portion.

The apparatus is preferably configured such that, in use, the angle of incidence of the beamlets on the front surface is within 3 degrees of normal incidence.

Preferably, the spatial sampling element comprises a lenslet array. In certain embodiments the reflected or scattered light from the front surface and from the second surface or interface is captured with the spatial sampling element. In other embodiments the reflected or scattered light from the front surface and from the second surface or interface is captured with a second spatial sampling element.

Preferably, the apparatus comprises a processor for: producing, from the relative phase measurements, a map of relative phase across the illuminated portion of the cornea; and monitoring the relative phase over time to determine time variations in the map.

The apparatus preferably comprises an interferometer for interfering the reflected or scattered light from the front surface and from the second surface or interface with a reference beam, to generate one or more interferograms. Preferably, the processor is configured to utilise the one or more interferograms to track the location of the beamlets on the front surface, for registering two or more maps of relative phase acquired at different times.

In preferred embodiments the optical source comprises a multi-wavelength optical source, and the processor is preferably configured to calculate, from the map of relative phase, a tomographic profile of the cornea. The tomographic profile may comprise one or more of amplitude, phase or optical path length between the front surface and the second surface or interface. Preferably, the second surface or interface comprises the posterior surface of the cornea, such that the optical path length comprises a measure of corneal thickness.

In preferred embodiments the processor is configured to determine, from time variations in the optical path length, a biomechanical response of the cornea to relative differences between intraocular pressure and an external pressure on the cornea. In certain embodiments the processor is configured to determine a biomechanical response of the cornea to periodic intraocular pressure variations associated with the ocular pulse. In other embodiments the apparatus is configured to vary the external pressure on the cornea. In certain embodiments the apparatus is configured to vary the external pressure by applying a source of distributed sound waves, or by varying the ambient pressure at the cornea.

In certain embodiments the processor is configured to determine, from time variations in the optical path length, a biomechanical response of the cornea to a perturbation imposed by one or more of: an air puff source; a source of ultrasound; or a source of acoustic radiation pressure.

In certain embodiments the apparatus is configured to measure time variations in the thickness of a tear film on the cornea. Preferably, the processor is configured to: measure time variations in the thickness of a tear film on the cornea; and subtract the measured time variations in tear film thickness from the optical path length to provide a normalised measurement of corneal optical path length.

According to a second aspect of the present invention there is provided a method for measuring one or more properties of a cornea, said method comprising the steps of:
generating a converging array of beamlets configured to impinge simultaneously on at least a portion of a front surface of a cornea;
capturing reflected or scattered light from said front surface and reflected or scattered light from a second surface or interface of said cornea;
measuring relative phase between the reflected or scattered light from said front surface and the reflected or scattered light from said second surface or interface across the portion of said cornea illuminated by said beamlets; and
monitoring said relative phase over time to obtain information on one or more properties of said cornea across the illuminated portion.

Preferably, the method further comprises the steps of: producing, from the relative phase measurements, a map of relative phase across the illuminated portion of the cornea; and monitoring the relative phase over time to determine time variations in the map.

Preferably, the method further comprises the steps of: interfering the reflected or scattered light from the front surface and from the second surface or interface with a reference beam to generate one or more interferograms; and utilising the one or more interferograms to track the location of the beamlets on the front surface, for registering two or more maps of relative phase acquired at different times.

In preferred embodiments the beamlets are generated from a multi-wavelength optical source, and the map of relative phase preferably provides a tomographic profile of the cornea. The tomographic profile may comprise one or more of amplitude, phase or optical path length between the front surface and the second surface or interface. Preferably, the method further comprises the step of determining, from time variations in the optical path length, a biomechanical response of the cornea to relative differences between intraocular pressure and an external pressure on the cornea. In certain embodiments a biomechanical response of the cornea to periodic intraocular pressure variations associated with the ocular pulse is determined.

In certain embodiments the method further comprises the steps of: imposing on the cornea a perturbation comprising one or more of an air puff, ultrasound or acoustic radiation pressure; and determining, from time variations in the optical path length, a biomechanical response of the cornea to the perturbation.

In certain embodiments the method further comprises the step of measuring time variations in the thickness of a tear film on the cornea. Preferably, the measured time variations in tear film thickness are subtracted from the optical path length to provide a normalised measurement of corneal optical path length.

According to a third aspect of the present invention there is provided an apparatus for measuring one or more properties of a cornea, said apparatus comprising an optical system for:
generating a converging array of beamlets configured to impinge simultaneously on at least a portion of a first surface or interface of a cornea;
capturing reflected or scattered light from said first surface or interface and reflected or scattered light from a second surface or interface of said cornea;
measuring relative phase between the first and second surfaces or interfaces across the portion of said cornea illuminated by said beamlets; and
monitoring said relative phase over time to obtain information on one or more properties of said cornea across the illuminated portion.

In certain embodiments the optical system is configured to measure the phases of the first and second surfaces or interfaces relative to a reference beam. In other embodiments the optical system is configured to measure the phases of the first and second surfaces or interfaces relative to a reflection from a tear film on the cornea. The first surface or interface may comprise the air/tear film interface.

Preferably, the apparatus comprises a processor for: producing, from the relative phase measurements, a map of relative phase across the illuminated portion of the cornea; and monitoring the relative phase over time to determine time variations in the map. The optical system preferably comprises a multi-wavelength source for generating the beamlets, and the processor is preferably configured to calculate, from the map of relative phase, a tomographic profile of the cornea.

According to a fourth aspect of the present invention there is provided a method for measuring one or more properties of a cornea, said method comprising the steps of:
generating a converging array of beamlets configured to impinge simultaneously on at least a portion of a first surface or interface of a cornea;
capturing reflected or scattered light from said first surface or interface and reflected or scattered light from a second surface or interface of said cornea;
measuring relative phase between said first and second surfaces or interfaces across the portion of said cornea illuminated by said beamlets; and
monitoring said relative phase over time to obtain information on one or more properties of said cornea across the illuminated portion.

In certain embodiments the phases of the first and second surfaces or interfaces are measured relative to a reference beam. In other embodiments the phases of the first and second surfaces or interfaces are measured relative to a reflection from a tear film on the cornea. The first surface or interface may comprise the air/tear film interface.

Preferably, the method further comprises the steps of: producing, from the relative phase measurements, a map of relative phase across the illuminated portion of the cornea; and monitoring the relative phase over time to determine time variations in the map. Preferably, the beamlets are generated from a multi-wavelength optical source, and the map of relative phase preferably provides a tomographic profile of the cornea.

According to a fifth aspect of the present invention there is provided an apparatus for investigating a tear film on a cornea, said apparatus comprising:
an illumination system for illuminating a tear film or the anterior surface of a cornea at a plurality of points; and
a capture optical system for capturing return signals comprising hyper-reflective signals from said tear film or scattered light from said anterior surface at said plurality of points, said capture optical system having a capture angle,
wherein said illumination system is configured to, in use:
illuminate a first set of said plurality of points with light that impinges on said tear film or said anterior surface at an angle of incidence sufficiently close to normal incidence such that said hyper-reflective signals are within said capture angle, resulting in a set of higher intensity return signals; and illuminate a second set of said plurality of points with light that impinges on said tear film or said anterior surface at an angle of incidence sufficiently far from normal incidence such that said hyper-reflective signals are not within said capture angle, resulting in a set of lower intensity return signals;
and wherein said apparatus further comprises a processor for:
processing the higher intensity and lower intensity sets of return signals to obtain optical coherence tomography measurements; and
calculating, from selected optical coherence tomography measurements of the higher intensity and lower intensity sets of return signals, a measure related to the thickness of said tear film.

In certain embodiments the processor is configured to calculate the measure related to the thickness of the tear film by: fitting a surface to the optical coherence tomography measurements of the lower intensity set of return signals; and calculating differences between the surface and selected optical coherence tomography measurements of the higher intensity return signals. In other embodiments the processor is configured to calculate the measure related to the thickness of the tear film by: fitting a first surface to the optical coherence tomography measurements of the higher intensity return signals; fitting a second surface to the optical coherence tomography measurements of the lower intensity return signals; and calculating an offset between the first and second surfaces. The processor is preferably configured to monitor time variations in the measure related to the thickness of the tear film.

In certain embodiments the processor is configured to determine a boundary between the set of higher intensity return signals and the set of lower intensity return signals. The processor may be configured to obtain, from the size or shape of the boundary, or from time variations thereof, information on the thickness, quality or distribution of a lipid layer of the tear film.

Preferably, the illumination system is configured to illuminate the tear film or the anterior surface of the cornea simultaneously at the plurality of points. More preferably, the illumination system is configured to illuminate the tear film or the anterior surface of the cornea with an array of substantially parallel beamlets.

In preferred embodiments the illumination system is configured to illuminate the first set of points with light that impinges on the tear film or the anterior surface at an angle of incidence less than 15 degrees, more preferably less than 8 degrees, and most preferably less than 4 degrees.

In preferred embodiments the illumination system is configured to illuminate the second set of points with light that impinges on the tear film or the anterior surface at an angle of incidence greater than 4 degrees, more preferably greater than 8 degrees, and most preferably greater than 15 degrees.

According to a sixth aspect of the present invention there is provided a method for investigating a tear film on a cornea, said method comprising the steps of:
  illuminating said tear film or the anterior surface of said cornea at a plurality of points;
  capturing, with a capture optical system having a capture angle, return signals comprising hyper-reflective signals from said tear film or scattered light from said anterior surface at said plurality of points, wherein a first set of said plurality of points is illuminated with light that impinges on said tear film or said anterior surface at an angle of incidence sufficiently close to normal incidence such that said hyper-reflective signals are within said capture angle, resulting in a set of higher intensity return signals, and a second set of said plurality of points is illuminated with light that impinges on said tear film or said anterior surface at an angle of incidence sufficiently far from normal incidence such that said hyper-reflective signals are not within said capture angle, resulting in a set of lower intensity return signals;
  processing the higher intensity and lower intensity sets of return signals to obtain optical coherence tomography measurements; and
  calculating, from selected optical coherence tomography measurements of the higher intensity and lower intensity sets of return signals, a measure related to the thickness of said tear film.

In certain embodiments the calculating step comprises: fitting a surface to the optical coherence tomography measurements of the lower intensity return signals; and calculating differences between the surface and selected optical coherence tomography measurements of the higher intensity return signals. In other embodiments the calculating step comprises: fitting a first surface to the optical coherence tomography measurements of the higher intensity return signals; fitting a second surface to the optical coherence tomography measurements of the lower intensity return signals; and calculating an offset between the first and second surfaces. Preferably, the method further comprises the step of monitoring time variations in the measure related to the thickness of the tear film.

In certain embodiments the method further comprises the step of determining a boundary between the set of higher intensity return signals and the set of lower intensity return signals. The method may further comprise the step of obtaining, from the size or shape of the boundary, or from time variations thereof, information on the thickness, quality or distribution of a lipid layer of the tear film.

Preferably, the tear film or the anterior surface of the cornea is illuminated simultaneously at the plurality of points. More preferably, the tear film or the anterior surface of the cornea is illuminated with an array of substantially parallel beamlets.

In preferred embodiments the first set of points is illuminated with light that impinges on the tear film or the anterior surface at an angle of incidence less than 15 degrees, more preferably less than 8 degrees, and most preferably less than 4 degrees.

In preferred embodiments the second set of points is illuminated with light that impinges on the tear film or the anterior surface at an angle of incidence greater than 4 degrees, more preferably greater than 8 degrees, and most preferably greater than 15 degrees.

According to a seventh aspect of the present invention there is provided an article of manufacture comprising a non-transitory computer usable medium having a computer readable program code configured to operate the apparatus according to the first, third or fifth aspects, or to implement the method according to the second, fourth or sixth aspects.

BRIEF DESCRIPTION OF THE DRAWINGS

Preferred embodiments of the invention will now be described, by way of example only, with reference to the accompanying drawings in which.

DETAILED DESCRIPTION OF THE INVENTION

Figure 1A:
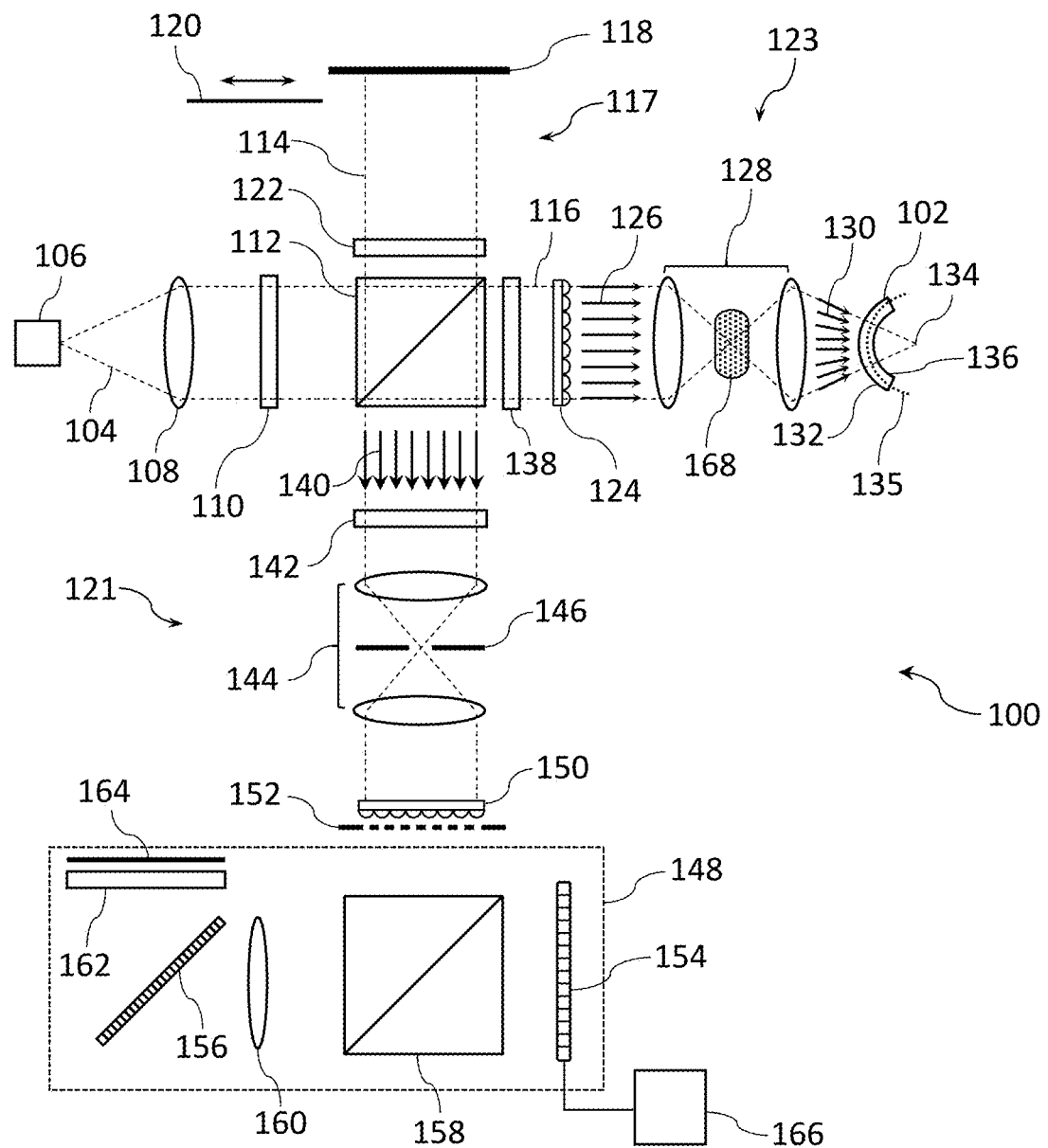
FIG. 1A illustrates in schematic form a spectral domain OCT apparatus for in-vivo measurement of one or more properties of a cornea at a plurality of points with phase accuracy, i.e. nm level accuracy, according to an embodiment of the invention.

FIG. 1A shows in schematic form a spectral domain optical coherence tomography (OCT) apparatus 100 suitable for in-vivo measurement of one or more properties of a human cornea 102 at a plurality of points with phase accuracy, i.e. nm level accuracy, according to an embodiment of the present invention. Light 104 from a broadband optical source 106 such as a superluminescent diode with centre wavelength 840 nm and bandwidth 40 nm is collimated by a collimating element 108 such as a lens or a parabolic mirror, linearly polarised by a polarizer 110 and then split by a polarisation beam splitting cube (PBS) 112 into reference and sample beams 114, 116. The reference arm 117 includes a mirror 118, a moveable shutter 120 for blocking the reference beam 114 if the apparatus is to be operated without the reference beam, and a quarter wave plate 122 for polarisation transformation so that light reflected from the mirror 118 passes through the PBS 112 and into the detection arm 121. The reference arm 117 may also include relay elements as well as dispersion matching components for compensating for the dispersion of optics in the sample arm 123. The mirror 118 may be moved axially to adjust the path length of the reference arm relative to the sample arm, e.g. to match different eye positions or to obtain information from structures at different depths in the eye. Alternatively or additionally, the entire apparatus 100 may be moved axially with respect to the cornea 102 to adjust the eye to apparatus distance and therefore the path length of the sample arm 123.

The sample arm comprises a quarter wave plate 138, a spatial sampling element in the form of a two-dimensional (2-D) lenslet array 124 to generate from the sample beam 116 a 2-D array of sample beamlets 126 which are relayed to the cornea 102 via a lens system 128. In the illustrated embodiment the lens system is non-telecentric, designed such that the central rays of the relayed beamlets 130 impinge on the anterior surface 132 of the cornea, or more precisely the air/tear film interface as explained below, at or close to normal incidence. The central rays of the converging array of relayed beamlets 130 may for example converge at a point 134 approximately 8 mm beyond a focal surface 135, i.e. beyond the surface where the beamlet waists lie. In preferred embodiments the lens system 128 is designed such that the focal surface 135 is substantially spherical as shown, with the convergence point 134 of the beamlets 130 approximately at the centre of curvature of this surface. In an alternative embodiment illustrated in FIG. 1B the sample arm includes a telecentric or 4F lens system 170 designed to produce an array of relayed beamlets 172 that propagate to the cornea 102 in substantially parallel fashion, in which case the focal surface of the beamlets will be substantially planar. For simplicity of illustration the lenses in the relay lens systems 128 and 170 are depicted as simple single element lenses, although in preferred embodiments they have multiple elements to reduce distortions of the relayed beamlets over the signal bandwidth. In yet another embodiment illustrated in FIG. 1C the sample arm includes a lens system 174 comprising a conventional lens 176 and a compound lens 178. The compound lens comprises a shorter focal length section that directs an inner subset of beamlets 130 onto the cornea 102 at normal or near-normal incidence, and a longer focal length section that directs an outer subset of beamlets 180 onto the anterior sclera 182 or the limbus 184.

Light scattered or reflected from the anterior or posterior corneal surfaces 132, 136, or from other interfaces in the cornea 102 or from deeper eye structures, passes back through the relay lens system 128, 170 or 174, then is captured by the lenslet array 124 and reflected by the PBS 112 into the detection arm 121 following polarisation transformation at the quarter wave plate 138. In general the number of beamlets 126 that can be relayed onto the cornea 102 depends on the design of the 2-D lenslet array 124, and in certain embodiments there may for example be of order 100 or 1000 beamlets in a square or rectangular pattern with a density of, say, 4 to 100 beamlets per square millimetre at the nominal focal surface 135, i.e. at the waists of the beamlets 130 or 172. In use the apparatus will preferably be positioned such that the nominal focal surface 135 is within or very close to the cornea 102, as shown in FIG. 1A. To enhance the relatively weak reflection from the posterior corneal surface 136 it may be further preferred for the nominal focal surface 135 to be close to the posterior corneal surface 136.

If the reference beam 114 is present it is combined with the reflected sample beamlets 140 at the PBS 112 and the resulting combined beams analysed by a polarizer 142 to interfere the light from the sample and reference paths. If the reference beam 114 is blocked by the shutter 120, an interference signal can arise between light reflected or scattered from two or more surfaces or interfaces in the eye, such as the air/tear film interface and the posterior corneal surface 136. Whatever the source of the interference signal, the resultant interference pattern, containing information on relative phase between light reflected or scattered from two or more surfaces or interfaces in the eye, is relayed by a system of lenses 144, and an optional aperture 146 to remove stray light, for spectral analysis in a spectrometer 148 at a grid of spatial positions determined by a spatial sampling element in the form of a 2-D lenslet array 150, and a corresponding 2-D aperture array 152.

The spectrometer 148 is able to analyse a plurality of grid points, beams or beamlets simultaneously, or at least within a single frame of a 2-D sensor array 154, for snapshot acquisition. After entering the spectrometer 148 the interfered beamlets are redirected by a PBS 158 to a lens 160 that collimates the beamlets for dispersion by a grating 156, followed by double passage through a quarter wave plate 162 via reflection from a mirror 164 to rotate the polarisation state by 90 degrees. The dispersed spectral components are imaged by the lens 160 onto a 2-D sensor array 154 such as a CMOS camera after passing through the PBS 158, for extraction or measurement of relative phase between light reflected or scattered from two or more surfaces or interfaces in the eye, in particular from two or more surfaces or interfaces in the cornea or tear film. In preferred embodiments the grating 156 is oriented with respect to the grid of spatial positions determined by the 2-D lenslet array 150 and the corresponding 2-D aperture array 152 such that each of the combined beamlets entering the spectrometer 148 is dispersed onto a separate set of pixels of the 2-D sensor array 154, as described in published US patent application No US 2016/0345820 A1 entitled 'High resolution 3-D spectral domain optical imaging apparatus and method', the contents of which are incorporated herein by reference. As explained in more detail below, the relative phase between light reflected or scattered from two or more surfaces or interfaces in the cornea or tear film, or more succinctly the relative phase between two or more surfaces or interfaces in the cornea or tear film, can be monitored over time in a series of snapshot measurements at the 2-D sensor array 154 to obtain information on one or more properties of the cornea 102.

In certain embodiments the sample arm relay system 128, 170 or 174 also includes a scanning element 168 such as a MEMS mirror for translating the array of relayed beamlets 130 or 172 across the cornea 102 in one or two dimensions, e.g. to create a dense map across a substantial portion of the cornea by 'filling in' the gaps between the beamlets of the beamlet array. This dense map, which is preferably time averaged over many snapshots to average out time-dependent contributions to the measured thickness such as from tear film dynamics and heartbeat-related IOP fluctuations, can be used as a reference or template for correcting eye motion artefacts as described below. For simplicity of illustration the MEMS mirror 168 is shown as being transmissive rather than reflective.

Several variations on the apparatus 100 shown in FIG. 1A are possible. For example the splitting and recombining of the sample and reference beams 116, 114 could be effected with an optical fibre coupler or a non-polarising beam splitter, or the 2-D array of sample beamlets 126 could be generated by a spatial sampling element in the form of an aperture mask, a MEMS mirror array or a diffractive optical element rather than a lenslet array 124. In yet another variation a spatial sampling element in the form of a 1-D lenslet array or similar could be used to generate a 1-D array of sample beamlets, although in general a 2-D array is preferred for obtaining data across a larger area of the cornea 102 in a single frame. It will be appreciated that, as shown in FIG. 1D, an array of sample beamlets 126 could alternatively be formed with a first lenslet array 124 or other spatial sampling element placed before the beamsplitter 112, and reflected signals captured with a second lenslet array 124-A or other spatial sampling element located after the beamsplitter 112 in the detection arm 121. In yet another variation the lenslet array 124 is omitted so that the cornea 102 is illuminated with an unstructured wavefront, although in general for reasons of improved collection efficiency and reduced cross-talk from multiple scattering it is preferable to illuminate the cornea with a plurality of discrete beamlets.

Figure 2:
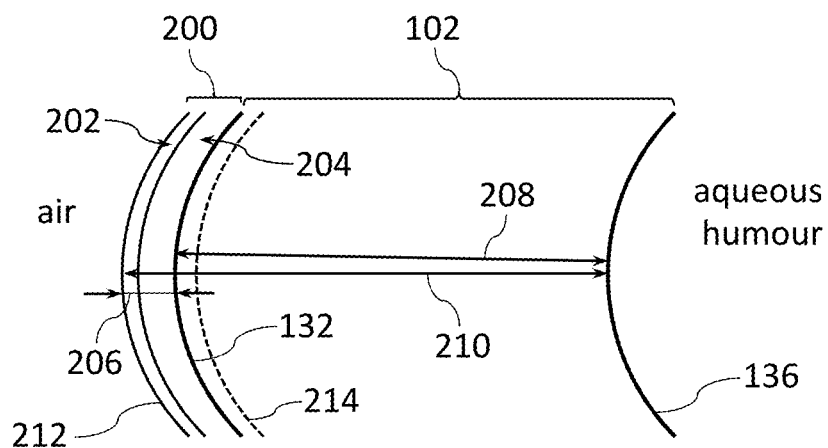
FIG. 2 shows in schematic form the structure of a tear film and a human cornea.

When measuring an eye in-vivo the cornea 102 is invariably covered with a tear film, in which case the first reflection will be from the air/tear film interface. As shown schematically in FIG. 2 the tear film 200 has multiple layers including a thin outer lipid layer 202 and an aqueous layer 204 that contacts the anterior surface 132 of the cornea 102 via a mucous layer (not shown). It should be noted that the thickness 206 of the tear film is exaggerated relative to the thickness 208 of the cornea. The main reflective surfaces of the corneal structure are summarised in Table 1, with the nominal Fresnel reflections at normal incidence calculated from the relevant refractive indices. In reality the air/tear film reflectivity is dominated by the aqueous layer because the lipid layer is so thin, and is generally a little above 2% at normal incidence with the strength modulated by the structure and thickness of the lipid layer 202. This is clearly still the most intense reflection, but reflections can also be detected from other surfaces or interfaces including the posterior corneal surface 136 and possibly also from intra-corneal structures such as Bowman's layer 214. For the purposes of this specification and the appended claims the term 'front surface of the cornea' means either the air/tear film interface 212 or the actual anterior surface 132 of the cornea 102, depending on whether a tear film 200 is present. The term 'anterior surface of the cornea' refers specifically to the physical front surface 132 of the cornea, i.e. the tear film/epithelium interface.

TABLE 1

| Structure | Nominal refractive index (visible) | Nominal thickness/ μm | Nominal Fresnel reflection at normal incidence |
|---|---|---|---|
| air | 1 | — | — |
| lipid tear layer | 1.48 | 0.05 | 3.75% |
| aqueous tear layer | 1.337 | 6 | 0.26% |
| cornea | 1.376 | 550 | 0.0207% |
| aqueous humour | 1.336 | — | 0.0218% |

Recalling that the interference signal from the cornea 102 contains information on relative phase between light reflected or scattered from two or more surfaces or interfaces in the cornea 102 or tear film 200, as mentioned previously the relative phase can be monitored over time in a series of measurements to obtain information on one or more properties of the cornea 102. In preferred embodiments the interferogram detected by the 2-D sensor array 154 is read out in a single frame for subsequent analysis by a processor 166 equipped with suitable computer readable program code, to obtain spatially resolved measurements, i.e. a map, of the cornea 102 across the portion illuminated by the beamlets 130. By reading out the sensor array 154 in a series of frames or snapshots over time, the processor 166 is able to monitor relative phase over time to determine time variations in a map of relative phase, for obtaining information on one or more properties of the cornea such as thickness or a biomechanical response, e.g. strain. In certain embodiments the processor 166 applies well-known Fourier transform-based OCT techniques to obtain a map of the cornea 102 in the form of a depth-resolved image, also known as a tomogram or tomographic profile. The tomogram may for example comprise one or more of amplitude, phase or optical path length between two or more corneal or tear film surfaces or interfaces, at a grid of points determined by the positions of the relayed beamlets 130 on the cornea 102. It will be appreciated that the optical path length between two corneal or tear film surfaces or interfaces is approximately equal to the product of the physical distance between those surfaces or interfaces and the effective refractive index, generally with a small offset due to phase changes related to the reflections.

In certain embodiments the spectral domain OCT apparatus 100 illustrated in FIG. 1A is employed in a snapshot multiprobe interferometric technique for in-vivo determination of very small temporal variations, on the nm scale, of corneal thickness at multiple points over the cornea 102, and for registering the position of the measurements on the cornea. Spatially resolved information on corneal biomechanical response, such as a measure related to Young's Modulus, can then be obtained from the measured thickness variations, e.g. by a finite element analysis. Although it has been shown to be possible to resolve the tear film 200 over a range of thicknesses with OCT using a sufficiently broad spectrum light source 106, see dos Santos et al *Optics Express* 23(16), 21043 (2015) for example, the tear film thickness 206 was close to their axial resolution limit of ~1 μm, which is not ideal for measurements of spatial or temporal thickness variations. Consequently, in preferred embodiments we measure the corneal/aqueous humour interface 136 relative to the air/tear film interface 212, i.e. the combined tear film+corneal thickness 210, and track variations in this combined thickness over time in a sequence of frames. In the absence of external pressure changes or perturbations, in general a plot of combined thickness 210 versus time will show a gradual decrease over several seconds between blinks due to tear film flow or evaporation, with superimposed periodic fluctuations on the ~1 second timescale due to the corneal strain response to the ocular pulse. These sources of temporal variation are uncorrelated and can be separated for example using standard curve fitting and subtraction techniques.

In a preferred embodiment a number of pachymetry maps, i.e. measurements of tear film+corneal thickness 210 at multiple points across the cornea, are acquired at an appropriate frame rate over several seconds. After accounting for the on-eye positions of the pachymetry maps in the data analysis as described below, the tear film variation is separated from the periodic heartbeat-related fluctuations to provide a map of corneal deformation versus time that can be correlated with the heartbeat. A typical rate of change of tear film thickness of about 1 μm over five seconds would correspond to a phase variation of a fringe of approximately 1.7 degrees per frame at a 100 Hz frame rate. As such there is generally no concern with phase wrapping issues, and the precision of the measurement can be maintained by tracking the phase over time. Consequently we can detect spatial variations in corneal elasticity through ultrasensitive in-vivo measurements of the periodic corneal biomechanical response to IOP fluctuations induced by the flow of blood synchronous with the heartbeat.

In other embodiments the apparatus or method can be used to provide spatially resolved information on a corneal biomechanical response to an external stimulus such as ultrasound, an air puff or acoustic radiation pressure. Such external stimuli are generally localised. Alternatively the apparatus or method can be used to provide spatially resolved information on a corneal biomechanical response to a distributed stimulus such as changing ambient air pressure or a source of distributed sound waves. The ambient pressure on the cornea may for example be varied via goggles or similar placed over the eye being measured. The apparatus or method may also be applied to monitor changes in biomechanical response over longer time frames, e.g. for detecting long-term corneal degradation or for gauging the effectiveness of clinical crosslinking treatments designed to increase corneal stiffness.

In certain embodiments pachymetry maps are generated with the apparatus 100 operated as a standard Michelson interferometer, with reflections from various interfaces such as the air/tear film interface 212 and the posterior corneal surface 136 referenced against the reference beam 114. However in preferred embodiments the apparatus 100 is operated as a common path interferometer with the reference beam 114 blocked, instead using the reflection from a front surface of the cornea, generally the air/tear film interface 212, as the reference for reflections or scattering from other interfaces or surfaces, preferably including the posterior corneal surface 136. We note that the phase and intensity of the reflected 'reference' light can be influenced by the lipid layer thickness and variations thereof, an effect that can be modelled if necessary. Since the thin lipid layer 202 will tend to influence the intensity of the average tear film reflection at the employed wavelength band, an accurate calibration of reflection intensity versus the slope of the cornea relative to an incident beam for a known reflection is also able to provide information on the lipid layer thickness. Although common path interferometry has slightly inferior signal-to-noise than standard interferometry, it has excellent phase stability as well as low noise during phase measurements, providing high measurement accuracy. Furthermore the common path interferometer measurements are virtually unaffected by axial eye motion since all of the interfaces being measured move together.

In preferred embodiments pachymetry maps are generated using an array of converging beamlets 130 as shown in FIG. 1A, i.e. with beamlets impinging on a front surface of the cornea 102 at substantially normal incidence. That is, the angle of incidence of the central rays of the beamlets 130 on a front surface of the cornea 102 is preferably within 3 degrees, more preferably within 2 degrees, and most preferably within 1 degree of normal incidence. This is particularly important with the common path interferometry configuration since it provides a consistent specular reflection over a large portion of the cornea against which reflections from other interfaces or surfaces can be referenced. Specular reflections could be captured from beamlets impinging on the cornea at other angles, but this would require additional optics to capture the reflected beamlets. The preferred combination of common path interferometry and a converging beamlet array at substantially normal incidence enables spatially resolved measurement of phase-resolved corneal thickness with sufficient sensitivity for detecting very small changes in corneal thickness and hence small changes in corneal elasticity.

Figure 1B:
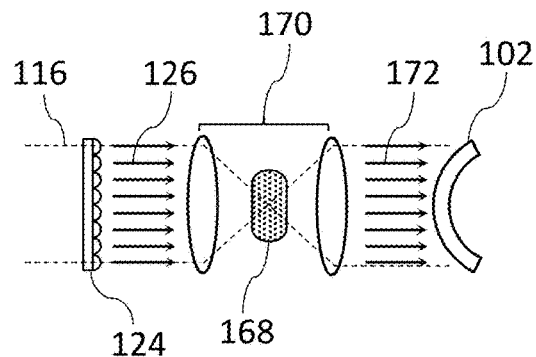
FIG. 1B illustrates in schematic form an alternative configuration of sample arm optics for the OCT apparatus of FIG. 1A.

In alternative embodiments pachymetry maps are generated using an array of substantially parallel beamlets 172 as shown in FIG. 1B, although the signal strength from the interfaces of interest is generally strongly attenuated beyond the apex of the cornea because the strong specular reflections are not captured, compromising the accuracy of the phase measurements. When using conventional OCT an additional difficulty is that the strength of the tear film reflection at the corneal apex is often comparable to the strength of the reference beam 114, possibly resulting in multiple phantom reflections that can complicate accurate reconstruction of the scattering profile. This is especially true if the signal strength causes saturation of the detector. In conventional OCT it is generally preferred to interfere a weak reflected signal from a sample with a stronger reference signal to provide both phase and depth information from each of the scattering points in an A-scan. As described below, however, probing the eye with an array of substantially parallel beamlets 172 may provide additional information on the tear film, including thickness and quality of the lipid layer.

Although eye motion has minimal effect on phase stability when measuring a pachymetry map of a cornea with the apparatus 100 configured for common path interferometry, it can still affect the measurement accuracy. For example changes in axial position of the eye relative to the apparatus will affect the apparent curvature of the corneal surfaces. Furthermore because the thickness of a healthy cornea increases gradually from the apex to the periphery, typically varying by ~100 μm over a 4 mm radius, a lateral variation in beamlet position of about 40 μm, e.g. from translation or rotation, would result in a corneal thickness variation of ~1 μm. Both these effects must be compensated for to ensure submicron accuracy of the resultant interferometric corneal pachymetry. In preferred embodiments the location of the tear film surface in a series of pachymetry maps is tracked by introducing a weak reference beam 114 for one or more conventional interferometry measurements. This enables registration of the pachymetry maps, which in turn allows correction of phase variations related to the eye motion. The frequency with which these conventional interferometry measurements are acquired, relative to the frequency of the common path interferometry measurements, can be chosen according to circumstances such as degree of eye movement or required measurement accuracy. For adequate registration of the common path pachymetry maps, in most cases it will suffice to acquire the conventional interferometry measurements occasionally, e.g. once every five, ten or twenty pachymetry measurements, optionally with interpolation of corrections across individual pachymetry measurements between successive registration measurements. To avoid saturating the sensor array 154 the intensity of the reference beam 114 in the registration measurements is preferably weaker than the intensity of the captured reflections for each beamlet, e.g. ~1% compared to the ~2% specular reflection from the tear film.

Figure 3:
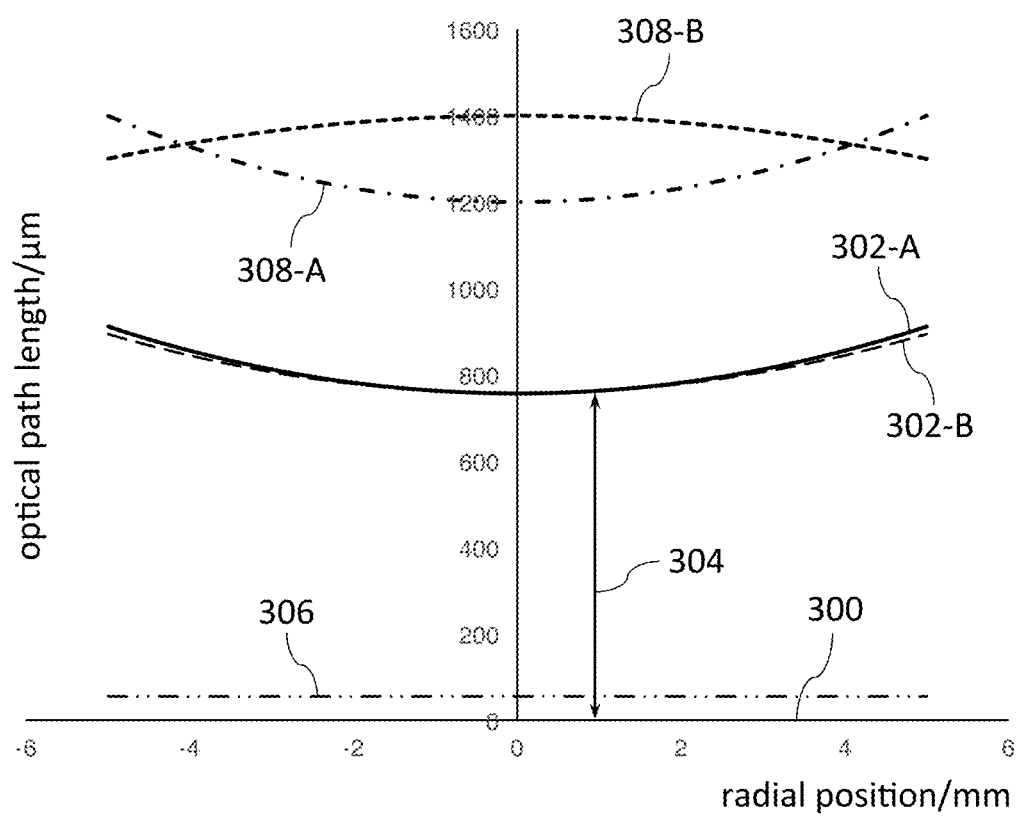
FIG. 3 illustrates the effect on apparent corneal thickness of changes in eye-to-apparatus axial position.

The registration process is explained with reference to the simulated interferometric data plotted in FIG. 3, which shows how changes in eye-to-apparatus axial position, caused for example by eye motion, can affect the apparent curvature of various corneal interfaces. In FIG. 3 the x-axis represents radial position from the corneal apex in mm, while the y-axis represents optical path length from the location 300 of the front surface, generally the air/tear film interface 212, in m. With the apparatus 100 configured for common path interferometry, the location of the posterior corneal surface 136 relative to the front surface is measured as a function of radial position for two different eye-to-apparatus axial positions, resulting in the traces 302-A and 302-B. Since the location 300 of the front surface coincides with the x-axis, the traces 302-A and 302-B represent a measure of optical path length thickness 304 of the cornea as a function of radial position, as may be measured with a one-dimensional array of beamlets, although as mentioned previously the array of beamlets is preferably two-dimensional. The trace 306 depicts Bowman's layer, another interface that may be measured with the apparatus 100 shown in FIG. 1A.

In principle the curvature of a trace such as 302-A or 302-B is indicative of the gradual increase in corneal thickness away from the apex, however it will be appreciated from the slight difference in curvature between these two traces 302-A and 302-B that variations in eye-to-apparatus axial position will affect corneal thickness measurements. When the apparatus 100 is re-configured for conventional interferometry using the reference beam 114, the location of the front surface of the cornea is measured for each of the two eye-to-apparatus axial positions, resulting in the traces 308-A and 308-B. Importantly, the curvature of these traces 308-A and 308-B, which represents the apparent curvature of the front surface of the cornea relative to the planar reference mirror 118, depends on the optical path length difference between the reference and sample paths, and is therefore sensitive to the eye-to-apparatus axial position. Consequently the difference in curvature between these traces 308-A and 308-B enables a correction to be calculated and applied to the apparent difference in curvature between the traces 302-A and 302-B. In FIG. 3 the traces 308-A and 308-B have been displaced in the y-axis relative to the other traces for convenience of display, but in reality the actual relative positions between the various traces are used in calculating the correction.

Although for simplicity FIG. 3 only illustrates the effect on corneal thickness measurements of changes in eye-to-apparatus axial position, the same principle applies to the correction of changes in curvature, shape or slope of the interferometric traces caused by translation or rotation of the eye relative to the apparatus. Once the position of the eye has been registered to the apparatus using the registration frames acquired using conventional interferometry, slight variations in apparent corneal thickness arising from eye motion can be corrected. If necessary, smaller terms in the distortion due to changes in the angles of incidence of the beamlets on a front surface of the cornea can be accounted for using geometry and Snell's law. It can be advantageous for the registration frames, at least, to include data from the anterior sclera 182 or the limbus 184, using the lens system 174 shown in FIG. 1C for example, to assist in accounting for both displacement and rotation as explained in published PCT patent application No WO 2018/136993 A1 entitled 'Optical coherence metrology and tomography with improved registration'.

The above-described registration procedure, based on additional measurements using the reference beam 114, is not needed if the corneal measurements are acquired using conventional interferometry rather than common path interferometry, although the positional information of the beamlets on the eye still needs to be processed. The above-described registration procedure may also be omitted if the cornea can be registered to itself, e.g. using an existing accurate pachymetry map acquired using the MEMS mirror 168 as described previously, or if eye movement can be tracked with a camera and the MEMS mirror 168 adjusted to lock the position of the beamlets 130 on the eye to stabilise the individual measurements.

Figure 1C:
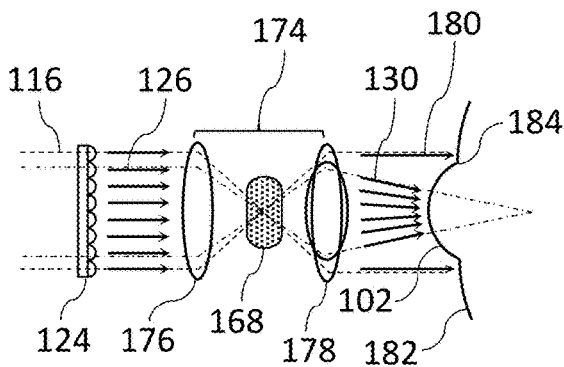
FIG. 1C illustrates in schematic form another configuration of sample arm optics for the OCT apparatus of FIG. 1A.
Figure 1D:
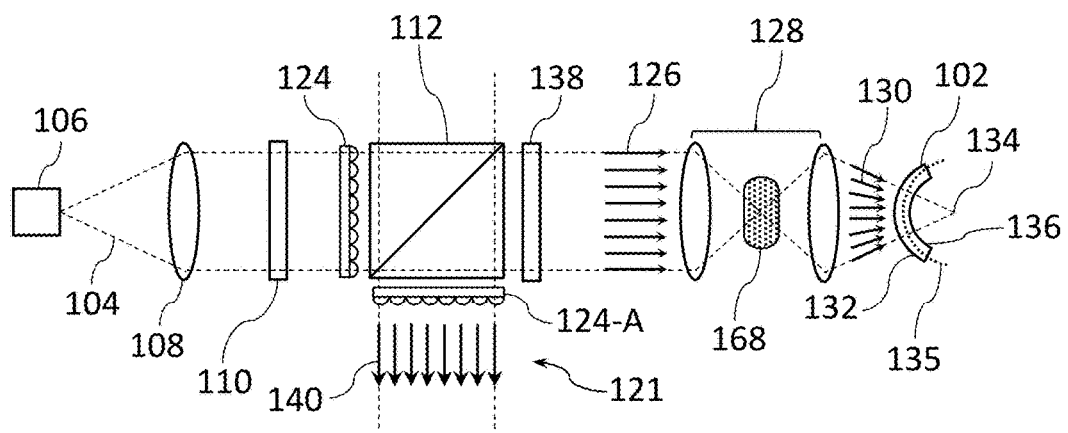
FIG. 1D illustrates in schematic form an alternative configuration for generating an array of beamlets and collected return signals.

A preferred procedure for in-vivo measurement of a corneal property such as thickness or biomechanical response using the apparatus 100 can be summarised as follows:

a) A map of the combined tear film+corneal thickness 210, i.e. a pachymetry map, represented by the interferometric trace 302-A, is produced with the reference beam 114 blocked, preferably using an array of converging beamlets 130 as shown in FIG. 1A or 1C although an array of substantially parallel beamlets 172 as shown in FIG. 1B may also be used.
   b) A map of the tear film location relative to the apparatus 100, represented by the interferometric trace 308-A, is produced with the reference beam 114 unblocked.
   c) For each subsequent pachymetry map measurement or group of measurements 302-B a new tear film location 308-B is ascertained.
   d) Based on the apparent change in tear film location, i.e. a comparison of the tear film traces 308-A and 308-B, a correction for eye motion can be calculated and applied to the later pachymetry map (or group of maps) 302-B. Any remaining differences between the pachymetry maps 302-B and 302-A can be assigned to actual changes in the cornea 102 or tear film 200.
   e) By acquiring additional pachymetry maps and correcting them for eye motion, changes in the combined tear film+corneal thickness 210 at a plurality of points across the cornea 102 can be tracked in time. The relative phase between light reflected from the air/tear film interface 212 and the posterior corneal surface 136 can be tracked without concern of phase wrapping if the pachymetry maps are acquired at a sufficiently high frequency, e.g. 100 Hz or more, for phase changes between measurements to be significantly less than $\pi$.
   f) The contributions to the time-varying pachymetry data of (i) tear film flow or evaporation and (ii) strain response to heartbeat-related IOP fluctuations or an external stimulus are analysed separately to provide spatially resolved information on both tear film dynamics and corneal biomechanical response. For example a gradual variation in tear film thickness 206 can be subtracted from the pachymetry data to provide a normalised measurement of corneal optical path length, i.e. thickness 208, and the strain response analysed to provide a measure related to Young's Modulus or some other stiffness or resilience-related parameter at a plurality of points across the cornea 102.

As the radius of curvature of the cornea varies from the apex towards the periphery, it is possible that the spectral reflection corresponding to a full map of the cornea cannot be captured within the numerical aperture of the lenslet array 124. A population-based correction to the focal surface 135 could be designed in the relay lenses, e.g. the lens system 128 in FIG. 1A. Alternatively the apparatus can be moved axially relative to the eye to optimise the capture of light reflected or scattered from regions of differing radii of curvature. The above embodiments have been described for the case where the apparatus 100 comprises a multi-wavelength optical source such as a broadband source 106 emitting light over a continuous band of wavelengths. This enables the acquisition of a tomographic profile of the cornea 102, preferably including a measure of corneal thickness. However information on one or more properties across a cornea can also be obtained by probing the cornea with an array of beamlets generated from a monochromatic source. Monochromatic light will only provide information on relative optical path length variations of the cornea 102 or tear film 200, either over time or between beamlets, and the return light may need to be monitored regularly to avoid phase wrapping artefacts. However the information on relative optical path length variations thus obtained may still be used in some low cost embodiments to infer a property such as relative strain or variations in tear film thickness 206 at a plurality of points across the cornea.

In other embodiments of the invention the apparatus 100 of FIG. 1A, with the high resolution lens relay 128 providing a specular reflection over a large area of a cornea 102, is used for determining tear film thickness dynamics, enabling absolute measurements of tear film thickness 206 with submicron accuracy and nm level relative precision significantly superior to those achievable with conventional OCT. With the reference beam 114 preferably blocked with the shutter 120, in certain embodiments the wavelength-resolved signals read out from the 2-D sensor array 154 by a suitably programmed processor 166 from each beamlet 140 reflected or scattered from the illuminated spots on the cornea 102 are each divided into, say, six or seven 5 nm wide wavelength bins over a number of successive frames. Data is preferably acquired over a period that allows at least one interferometric cycle, which corresponds to a tear film thickness change of greater than $\lambda/(2*n_{tear})$. For a broadband source 106 of centre wavelength $\lambda$=840 nm and assuming a tear film refractive index $n_{tear}$=1.337, this equates to a thickness change of at least 0.31 μm. The corresponding minimum data collection period can be estimated from the typical rate of thickness loss of the pre-corneal tear film 200 between blinks, and will generally be no more than a few seconds.

The processor 166 then calculates the temporal variation of the integrated power for each wavelength bin. Since the signal power within each bin will be relatively high because the return beamlets 140 have been specularly reflected from the cornea 102, it is possible to exploit the high signal-to-noise ratio and knowledge of the structure of the tear film 200 to achieve more accurate phase measurements. The combined reflected signal from the various tear film layers is the predominant signal that will not average out over the wavelength spread of the wavelength bins, so will have a variation dependent on the tear film thickness 206 as shown below. Even without numerical analysis, we can clearly identify the variation on a micron scale based on the spread of the time-dependent intensity plots for the wavelength bins. However to measure the profile of the tear film 200 over the cornea 102 we can also use phase information by tracking phase variations between spatial sampling points. In one particular example the 2-D lenslet array 124 and relay optics 128 provide sampling points on a 250 μm spaced square or rectangular grid at the nominal focal surface 135, i.e. at the waists of the beamlets 130.

Figure 4A:
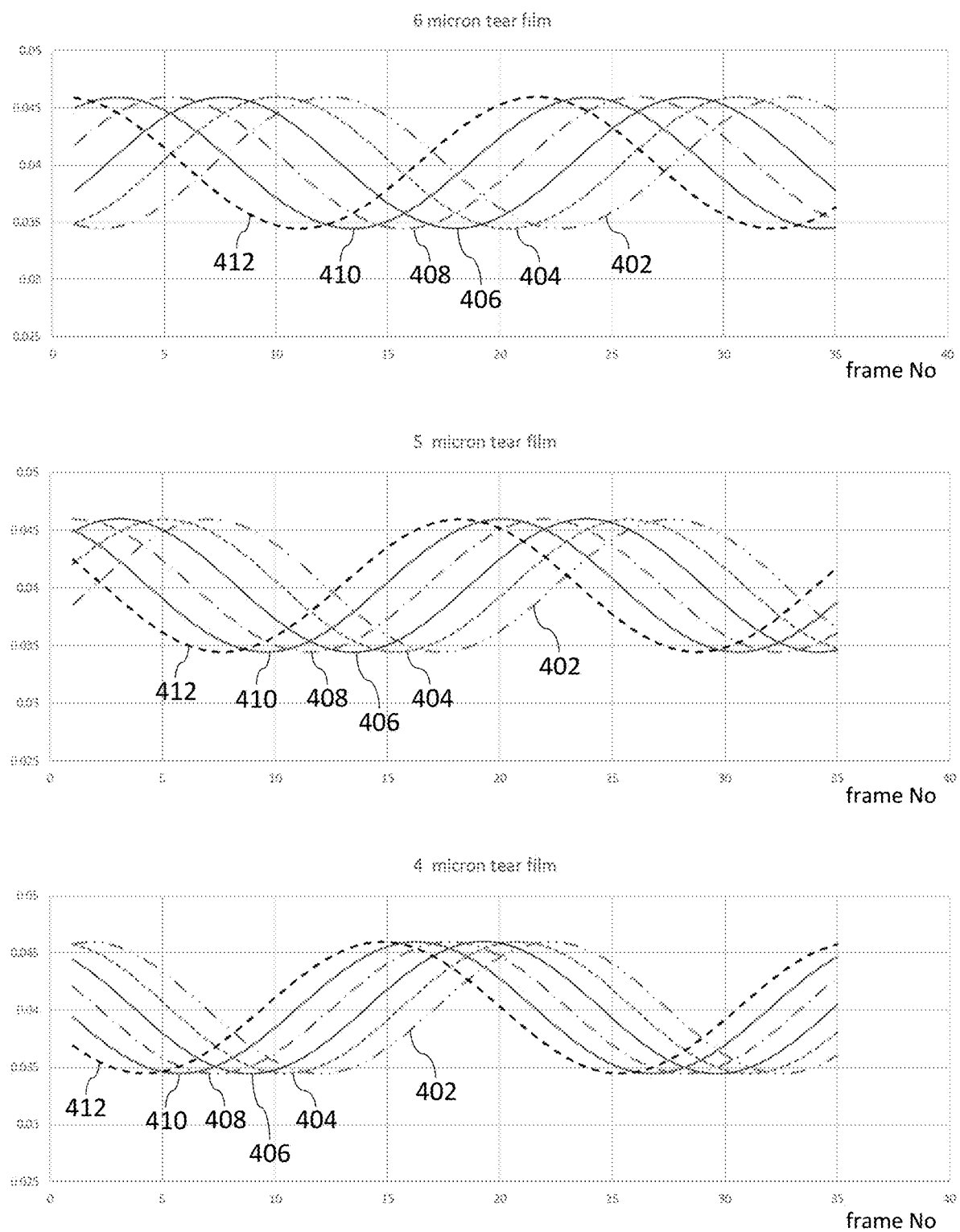
FIGS. 4A and 4B show, for six different starting tear film thicknesses from 6 μm to 1 μm, the expected time variation of reflected beamlet power in a number of discrete wavelength bins.
Figure 4B:
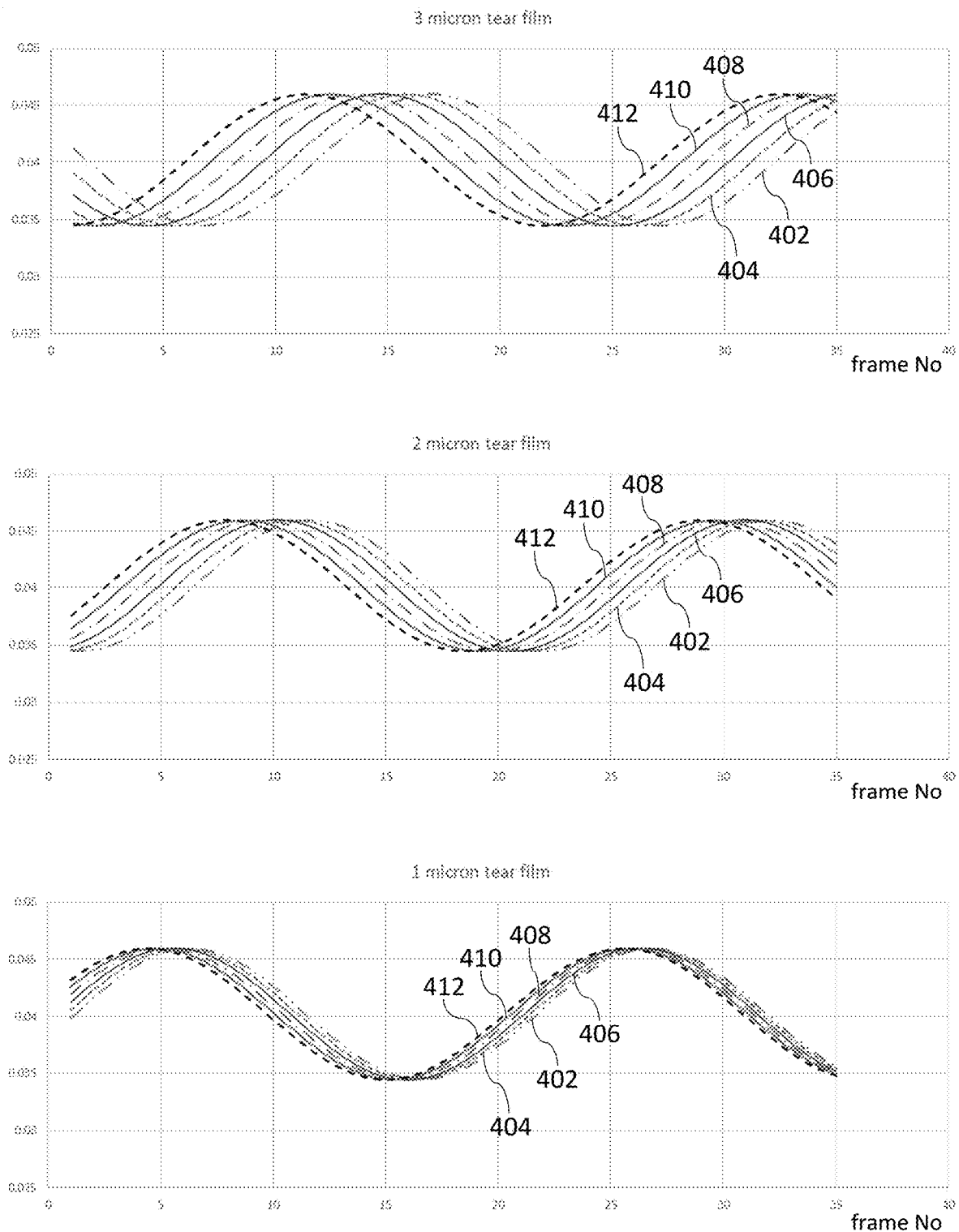

FIGS. 4A and 4B show, for six starting tear film thicknesses from 6 μm to 1 μm, plots 402, 404, 406, 408, 410 and 412 of the expected time variation of power in a reflected beamlet in each of six 5 nm wide wavelength bins centred on 0.82, 0.825, 0.83, 0.835, 0.84 and 0.845 m respectively, for an assumed constant rate of variation of tear film thickness 206. Each plot is calculated over 35 frames measured at a 10 Hz frame rate, i.e. over 3.5 seconds, with the power variations for each of the six wavelength bins moving through a little over one cycle during the measurement period.

Figure 5A:
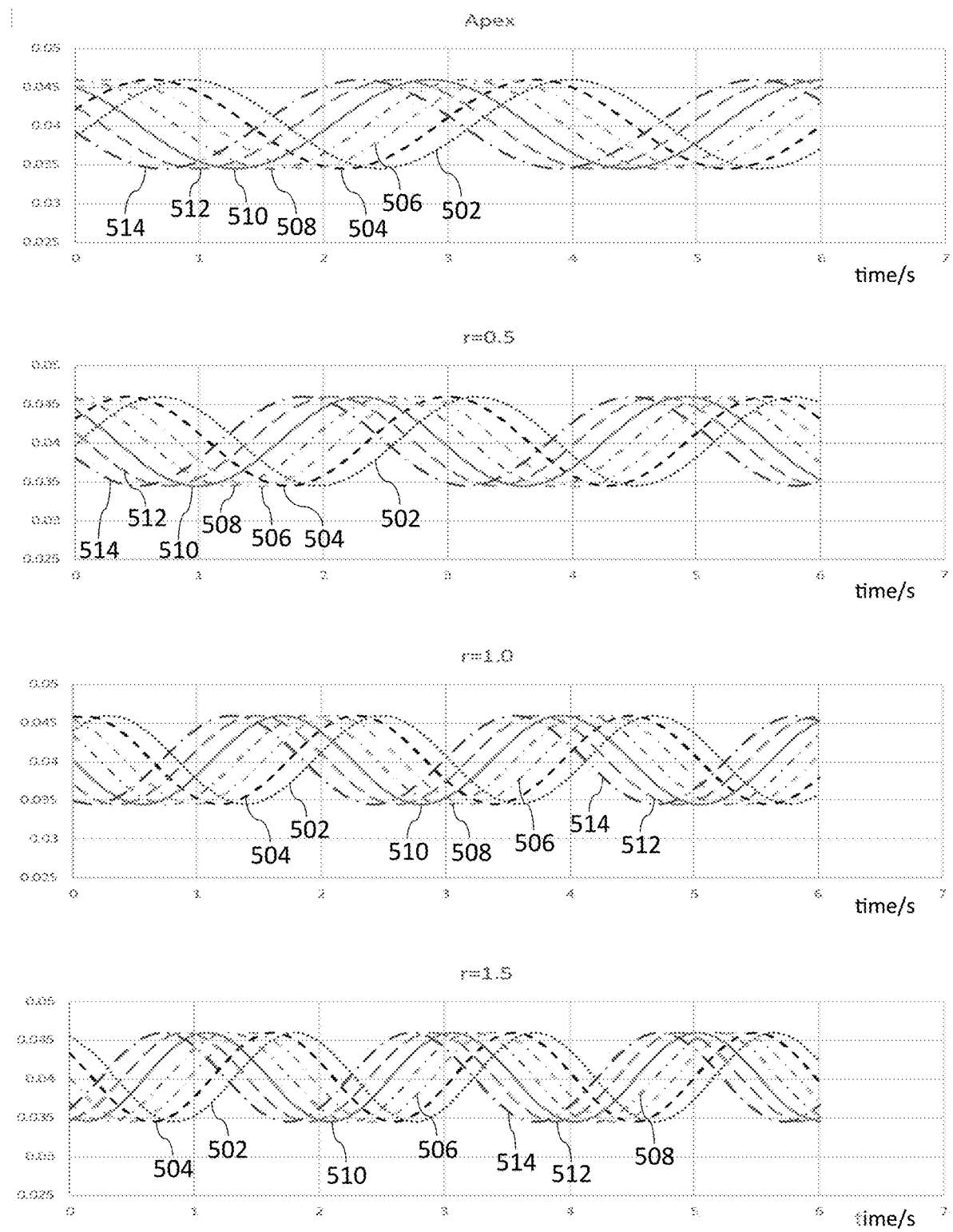
FIGS. 5A and 5B show, for seven radial positions from the corneal apex, the expected variation of power over six seconds, in a beamlet reflected from a tear film, in a number of discrete wavelength bins.
Figure 5B:
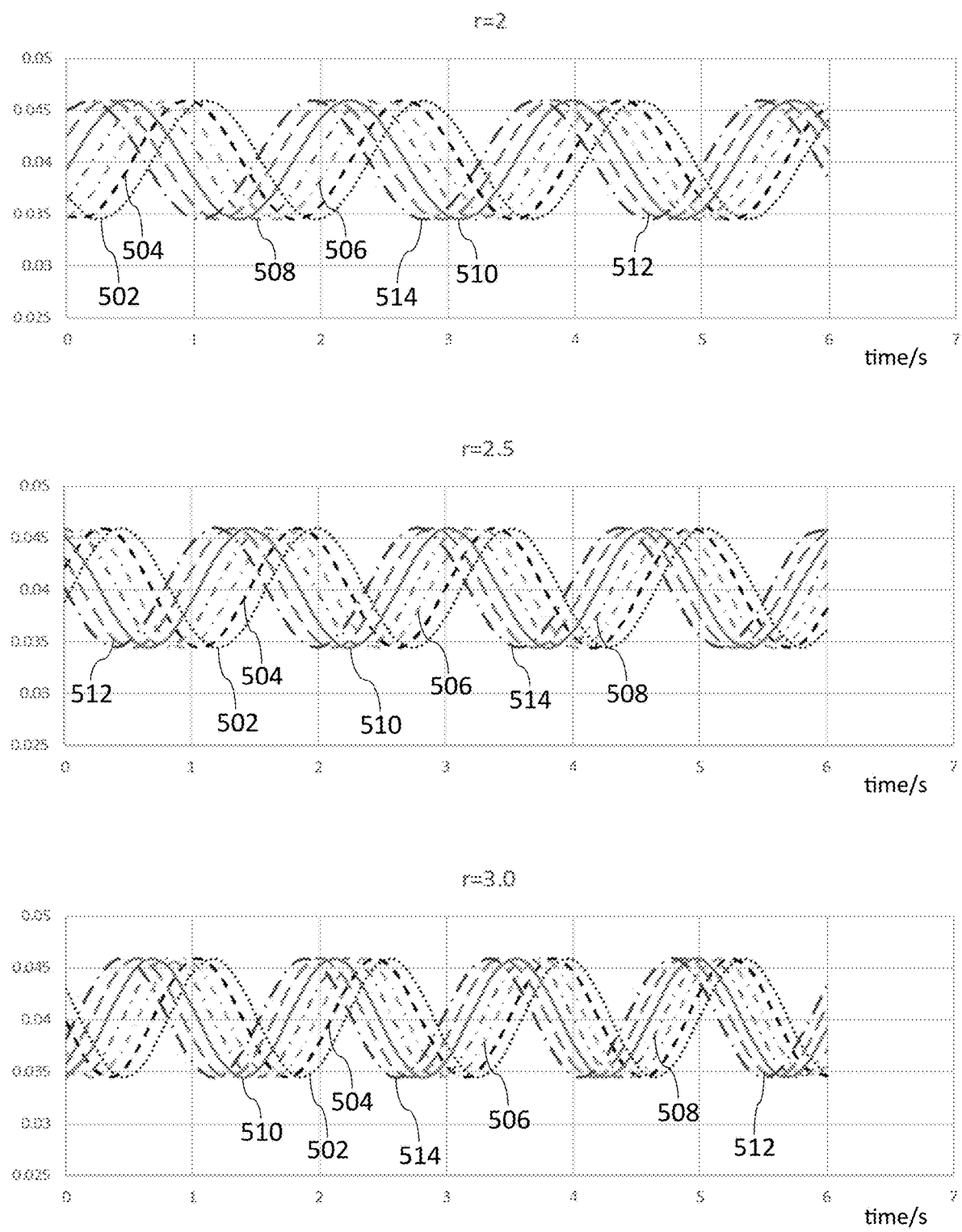

FIGS. 5A and 5B show, for seven radial positions r from zero to 3.0 mm measured from the corneal apex, plots 502, 504, 506, 508, 510, 512 and 514 of the expected variation of power in a reflected beamlet over six seconds in each of seven 5 nm wide wavelength bins centred on 0.82, 0.825, 0.83, 0.835, 0.84, 0.845 and 0.85 m respectively. These plots have been generated for a tear film 200 initially 5 μm thick at the apex (post-blink), with a model assuming a weak parabolic shape in tear film thickness 206 across the cornea and a rate of loss that increases with distance from the apex (r). These chosen assumptions are not necessarily realistic, although there is some evidence from fluorescein imaging of tear film dynamics that tear film breakup generally occurs away from the apex, implying either a smaller initial thickness or a higher rate of thickness loss. The main purpose of the assumptions is to show how variations in parameters such as rate of thickness loss can be revealed in this wavelength binning analysis. For example the temporal power variations in each wavelength bin for the r=3.0 mm plot can be seen to cycle more rapidly than in the plot at the apex.

Advantageously, with this approach the tear film dynamics at a particular position or region on the cornea 102 can be analysed robustly over time once we have a specular back reflection. For improved phase stability it is preferable for the measurements to be made with the reference beam 114 blocked, i.e. using common path interferometry, since the tear film thickness 206 is unlikely to be overly sensitive to slight variations in position resulting from eye motion. Alternatively the measurements may be made with a weak reference beam 114 present. The received signals can be normalised for coupling efficiency taking into account the power, relative positions of the beamlet waists and the angle of incidence on the tear film 200, as well as for the spectral profile of the light 104. The influence of the lipid layer 202, which will appear largely as an attenuation term since the bandwidth of its reflectivity profile will generally be much wider than that of the light source 106, can also be taken into account.

Figure 6:
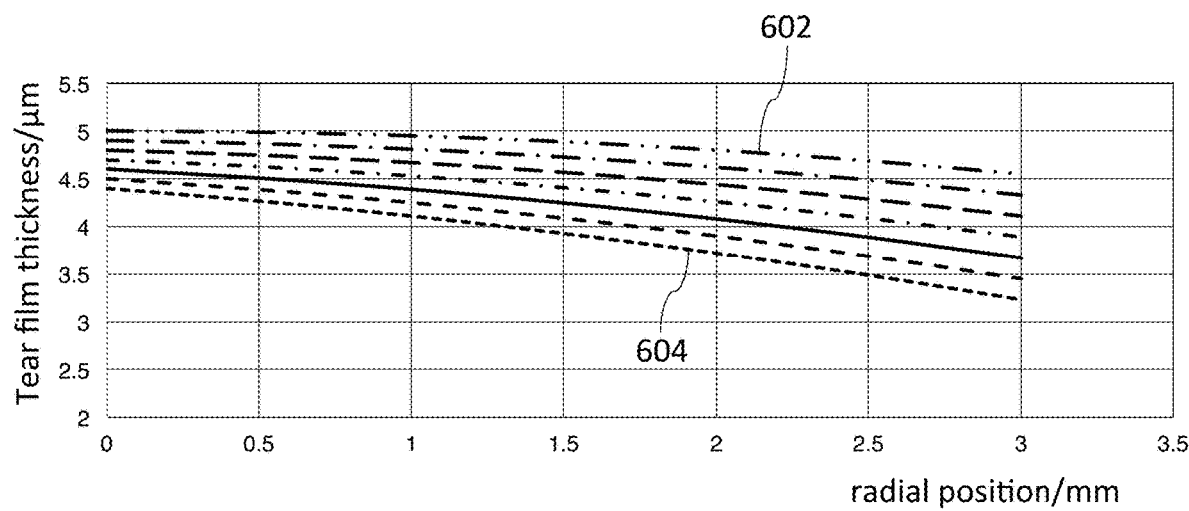
FIG. 6 depicts plots of tear film thickness versus radial position from the corneal apex at a number of different times from zero to six seconds after a blink.

The series of seven plots presented in FIGS. 5A and 5B have been calculated at radial positions spaced 0.5 mm apart in one axis only across the cornea, although a series of experimental measurements at intervals of 250 μm or less in two dimensions is achievable with the apparatus 100 depending on the design of the lenslet array 124 and the lens relay 128. Using the assumed continuity of tear film thickness 206 as a function of time and the small variation in tear film thickness over the radial position intervals, pathways of descending contours can be chosen with a phase shift of less than $\pi/2$ between sample points to remove any phase ambiguity, allowing us to obtain an unambiguous tear film profile over time with resolution limited only by the signal-to-noise ratio. Given the strong signals from the specular reflections in each spectral band or wavelength bin, we expect that the time evolution of tear film thickness 206 can be measured in-vivo with a precision of several nm. The previously described model, or some other model, can be applied to the data to determine the radial profile of the tear film 200 at different points in time. This is shown in FIG. 6, which depicts plots of tear film thickness in m versus radial position from the corneal apex in mm for t=0, 1, 2, 3, 4, 5 and 6 seconds following a blink, with the plots labelled 602 and 604 depicting the tear film profile at 0 and 6 seconds respectively.

The parameters of the chosen model can also be adapted to provide non-constant tear film dynamics and to identify tear film breakup. The chosen model also can include a factor to account for variation of the lipid layer thickness, which as mentioned previously will generally act to vary the strength of all of the spectral components over time.

The dynamics and profile of the pre-corneal tear film 200 are of interest in providing information regarding the impact of tear film quality and consistency on the refractive properties of the eye. The tear film profile, i.e. shape, is generally not captured in non-specular topographic OCT images, but is critical in determining refraction at the eye. Therefore the additional information on the tear film profile provided by our analysis can result in improved refraction estimates compared to those obtained purely from corneal topography.

It is worth noting that the detected return beamlets 140 could be analysed in the processor 166 using conventional OCT techniques, i.e. without the above-described wavelength binning analysis. For example the apparatus 100 may be configured for common path interferometry, with the air/tear film interface 212 providing the common path reference beam and the various layers of the cornea 102, such as the anterior or posterior surfaces 132, 136, providing smaller reflections that can be detected through the fringes. However because the tear film 200 typically has a thickness 206 of only a few microns, and because it can be important to measure tear film thickness down to the sub-micron level during breakup, a very wide spectrum would be required to separate the reflection peaks from the air/tear film interface 212 and the tear film/cornea interface 132. The required spectral width is well beyond the 40 nm bandwidth of the 840 nm light source 106 exemplified in the apparatus 100. In contrast the wavelength-binning analysis, which just requires a model with a priori information on the expected tear film structure and the temporal variation of the phase of light reflected from the tear-film/cornea interface 132, can provide tear film thickness 206 with sub-micron accuracy using an instrument with a much narrower spectrum, e.g. a 40 nm bandwidth. The same information could also be provided by analysis of the temporal variation of phase and intensity of the Fourier components of the return beamlets 140, especially the lowest few spectral Fourier components. For simplicity we have described the analysis in terms of a model of the wavelength-dependent fringes where the sensitivity to sub-wavelength shifts can be easily visualised and plotted, but this is not a limitation of the method.

Because the dynamics of the tear film variation are of the order of seconds and the frame rate of the spectrometer 148 is up to 300 Hz it is possible to increase the sampling density on the cornea by dithering the location of the beamlet array 130 in a pattern that repeats, say, at 5 Hz. For the case of a 250 µm 2-D grid spacing on the cornea 102 we can dither the beamlet array using the MEMS mirror 168 with a peak-to-peak equivalent displacement on the cornea of, say, 300 µm in an axis joining the grid points to provide a series of 'B scans' with some oversampling. This allows complete continuity of the phase between spatial points to be achieved while still allowing the tear film dynamics to be captured at 5 Hz. As a potentially useful benefit of this approach, it may be possible to derive a measure of the epithelium roughness or provide an epithelium profile under the reasonable assumption that the tear film thickness 206 is a smooth function of position before any breakup occurs, so that any microstructure observed in the series of B scans results from the underlying roughness of the tear film/epithelium interface 132. This information, which gives nm resolved roughness, can be of diagnostic value in refractive surgeries such as photorefractive keratectomy (PRK) where it is important to understand the regrowth of the epithelium and how that can influence the tear film and refraction of the eye.

To recover the topography of the anterior corneal surface 132 the time-averaged decay in tear film thickness is subtracted off the derived phase for each of the wavelength bins, noting that for a tear film thickness of several m at least some of the wavelength bin plots will generally have components in a sensitive region, i.e. away from a turning point, for most of the frames acquired. A measure of surface roughness or even a nano-topographic profile of the anterior corneal surface 132 can therefore be provided along with the tear film profile as a series of closely spaced B scans. It has been proposed, e.g. in King-Smith et al 'Tear film interferometry and corneal surface roughness', *Investigative Ophthalmology & Visual Science* 55(4), 2614 (2014), that variability or roughness of the corneal surface profile limits the ability to achieve a high level of contrast for interferometric spectral measurements, particularly in the visible to NIR. Notably, the use of small focused spots in the present invention, as well as the ability to ensure that the spot size is maintained by accurate positioning of the apparatus 100 relative to the tear film 200, via standard OCT with the reference beam 114, should help overcome this limitation. In some implementations it could be advantageous to utilise longer wavelength bands, say around 1550 nm, or have additional longer wavelength bands to enhance the contrast of the received signals.

Apart from providing information on the tear film dynamics, the wavelength binning method provides an alternative to the previously described curve fitting method for subtracting the contribution of the tear film thickness 206 from a pachymetry map, i.e. the combined tear film+corneal thickness 210 at a plurality of points across the cornea 102. This ensures that the phase variations of the pachymetry map can be normalised at each point in time to account for the thickness of the tear film, thus ensuring nm level precision of corneal thickness 208, which is important for elastography measurements of the cornea.

Figure 7:
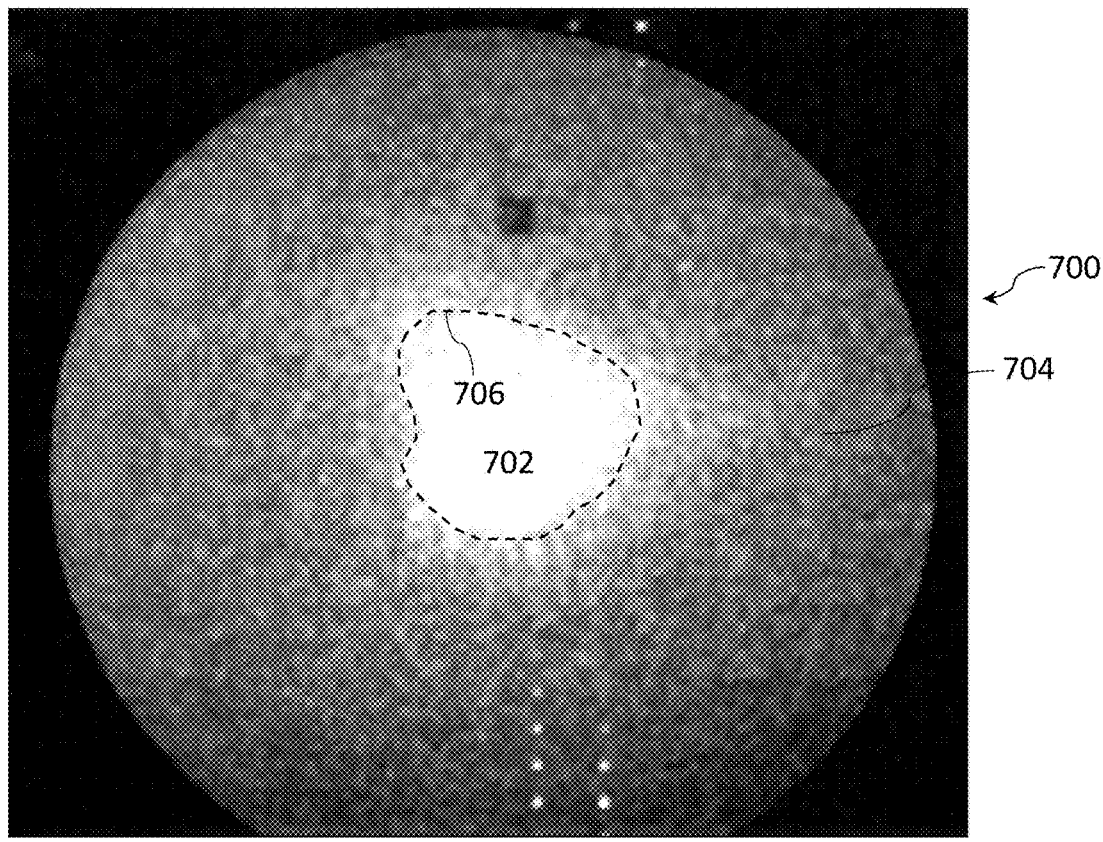
FIG. 7 shows an in-vivo reflectivity image of a portion of a cornea illuminated with an array of beamlets.

As explained previously, for measuring corneal thickness it is preferred to probe the eye using an array of converging beamlets 130 as shown in FIG. 1A, i.e. with beamlets impinging on a front surface of the cornea 102 at substantially normal incidence, to provide a consistent specular reflection over a large portion of the cornea against which reflections from other interfaces or surfaces can be referenced. Unexpectedly, we have found that probing the eye with an array of substantially parallel beamlets 172 as shown in FIG. 1B, which provides a large range of incidence angles on the cornea 102, is useful for studying the tear film 200 and in particular the lipid layer 202. FIG. 7 shows an in-vivo reflectivity image 700, approximately 2 mm in diameter, of a portion of the cornea of an eye obtained by illuminating a plurality of points with a 12×24 array of substantially parallel beamlets and integrating the reflected beamlet power over a depth range. The array of beamlets was generated using light from an (840±15) nm superluminescent diode sampled with a 2-D lenslet array, and extended across an area of approximately 11 mm×14 mm. The image 700 reveals a substantially binary intensity distribution with a highly reflective central region 702 and a rapid transition to a lower reflectivity outer region 704. The small dark square just above the higher intensity region 702 is an artefact caused by a defective camera pixel. The shape and size of the higher intensity region 702 varies between individuals and over time for an individual, a variability believed to be due to changes in the thickness, quality or distribution of the lipid layer 202.

In certain embodiments the reflectivity image 700 is processed to delineate the higher intensity inner region 702 and lower intensity outer region 704, e.g. using a bimodal segmentation algorithm with a chosen threshold, yielding a boundary 706. As shown schematically in FIG. 8, depth data 804-H, 804-L within the higher and lower intensity regions 702, 704 are calculated using standard optical coherence tomography techniques, e.g. from phase measurements relative to a reference beam 114, revealing a distinct transition 806 in elevation, typically of 1 to 6 μm, around the boundary 706. The magnitude of this transition 806, along with the fact that the substantially binary intensity distribution shown in FIG. 7 is not seen in test objects such as model eyes, strongly suggests the effect is related to the tear film. Consequently, differencing measurements between selected depth data 804-H, 804-L in the higher and lower intensity regions 702, 704 will provide a measure related to the thickness of the tear film. We note that elevation accuracies of better than 1 μm can be achieved, despite having an axial imaging resolution of around 10 μm, by finding edges using sub-pixel sampling techniques and fitting surfaces that allow averaging over a sufficiently large number of data points 804-H or 804-L.

In certain embodiments, first and second surfaces 800, 802 are fitted to depth data 804-H, 804-L in the higher and lower intensity regions 702, 704 respectively, allowing us to obtain a measure related to the thickness of the tear film from an offset 808 between the first and second surfaces 800, 802. In other embodiments a surface 802 is fitted to depth data 804-L in the lower intensity region 704, and differences between that surface 802 and selected depth data 804-H in the higher intensity region 702 provide a measure related to the thickness of the tear film.

Differences in elevation or offsets between the two surfaces 800, 802, or between the surface 802 and selected depth data 804-H, can be calculated at multiple locations, e.g. over the entire higher reflectivity region 702 or along the boundary 706, to provide spatially resolved measurements of tear film thickness over the region or boundary, which may be averaged to provide a single tear film thickness measurement. The tear film thickness measurements, averaged or otherwise, can then be used to calculate corrected corneal topography by offsetting the measured points 804-H in the inner region 702 with the tear film thickness before combining with the measured points 804-L in the outer region 704 and fitting a surface through the combined points. Advantageously, our edge-finding approach with the substantially binary intensity distribution obviates the previously noted difficulty that standard OCT image segmentation techniques have in separating the air/tear film interface from the tear film/cornea interface, given the typical axial resolution of 5 to 10 μm.

The substantially binary intensity distribution observed in FIG. 7 can be explained with reference to FIG. 9, which illustrates schematically the interaction of two substantially parallel beamlets 172-1, 172-2, represented by their central ray paths, with the lipid 202 and aqueous 204 layers of a tear film 200 and the anterior surface 132 of a cornea 102. As depicted schematically in FIG. 9 the lipid layer 202 is considerably more textured than the aqueous layer 204. In preferred embodiments the beamlets 172-1, 172-2 are two of a number of substantially parallel beamlets produced by the combination of a 2-D lenslet array 124 and a telecentric lens relay 170 as shown in FIG. 1B. One of the representative beamlets 172-1 impinges on the tear film 200 and cornea 102 at an angle of incidence 900 close to normal incidence, while the other representative beamlet 172-2 impinges on the tear film 200 and cornea 102 at an angle of incidence 902 that is significantly removed from normal incidence. For each beamlet a significant fraction of the light will experience a primarily specular reflection 904 from the tear film 200, within a cone or range of angles 906 determined largely by the textured nature of the lipid layer 202. A much smaller fraction of the light in each beamlet will be scattered at the anterior corneal surface 132, with this scattering 908 being essentially isotropic. In addition there will be a small amount of isotropic scattering from the lipid layer 202 and a weak specular reflection from the anterior corneal surface 132. These small components are not shown in FIG. 9, as they don't affect the explanation of the substantially binary intensity distribution seen in FIG. 7.

Referring to FIGS. 1A and 1i, it will be appreciated that the 2-D sensor array 154 will only detect return light from the cornea 102 or tear film 200 that is within the capture angle of the optical system used to capture return signals. Whether reflections 904 from beamlets 172 are detected is determined by the curvature of the cornea, i.e. the size of the sample eye, the numerical aperture of the beamlets 172 and the numerical aperture of the capture optical system, which in the illustrated embodiment comprises the lens relay system 170 and the lenslet array 124. For beamlets such as the representative beamlet 172-1 that impinge on the tear film 200 at an angle of incidence 900 sufficiently close to zero, i.e. close to normal incidence, the detected return signal will be dominated by the specular reflection 904 within the cone of angles 906, resulting in the bright central region 702 seen in FIG. 7. We shall refer henceforth to this brighter captured light from a combination of tear film surface structure and specular reflection as the hyper-reflective signal 910. On the other hand for beamlets such as the representative beamlet 172-2 that impinge on the tear film 200 at an angle of incidence 902 significantly larger than zero, i.e. far from normal incidence, the hyper-reflective signal 910 will not be captured and the main contribution to the detected return signal will be isotropic scattering 908 from the anterior corneal surface 132, resulting in the lower intensity outer region 704 seen in FIG. 7.

In alternative embodiments the reflectivity image 700 is processed with a segmentation algorithm having two thresholds. Data points with intensity above the higher threshold delineate the region 702 where the return signal is dominated by the lipid layer-influenced hyper-reflective signal 910, and may be used to fit a surface 800 corresponding to the air/tear film interface. Data points with intensity below the lower threshold delineate the outer region 704 where the return signal is dominated by scattering 908 from the anterior corneal surface 132, and may be used to fit a surface 802 corresponding to the anterior corneal surface 132. Data points with intensity between the two thresholds, which typically fall in a narrow band between the regions 702, 704, are not used when fitting either surface 800, 802. Once the tear film thickness has been determined, however, these intermediate points can be used as part of the height data by interpolating the offset based on their intensity relative to the two thresholds.

The observed variability in shape and size of the bright central region 702 between individuals, and over time for an individual, is thought to be due to changes in the thickness, quality or distribution of the lipid layer 202, which will affect the cone of angles 906 of the specular reflection 904 and therefore the hyper-reflective signal 910. Consequently the shape or size of the bright central region 702, as well as variations in the shape or size over time, may be a useful indicator of the thickness, quality or distribution of the lipid layer 202. Together with the tear film thickness, this may prove useful in distinguishing between different types of dry eye disease, such as aqueous deficient dry eye and evaporative dry eye for example.

In certain embodiments tear film break up or health are assessed via the dynamics of the derived thickness and topology in or of the hyper-reflectivity region 702. For example machine learning techniques such as Convolutional Neural Networks may be used in combination with large data-sets of both normal and diseased states of the eye to assist in the diagnosis and treatment of ocular conditions, in particular dry eye disease. An association between the intensity distribution seen in FIG. 7, including hyper-reflective signals from the tear film, on the one hand, and tear film and lipid layer health on the other hand, is anticipated to yield important correlations or predictive values once sufficiently large databases correlated with existing ocular health metrics have been established.

Figure 8:
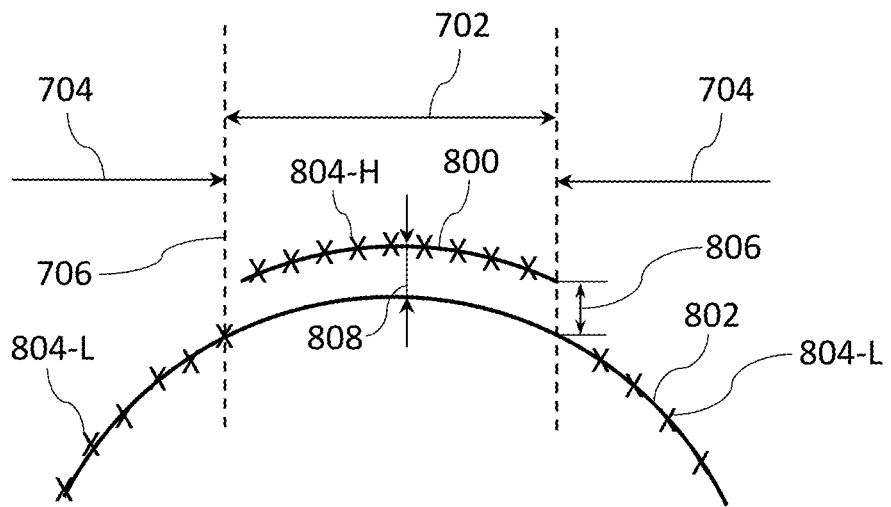
FIG. 8 depicts schematically a method for obtaining a measure related to tear film thickness using OCT data calculated across the reflectivity image of FIG. 7.
Figure 10:
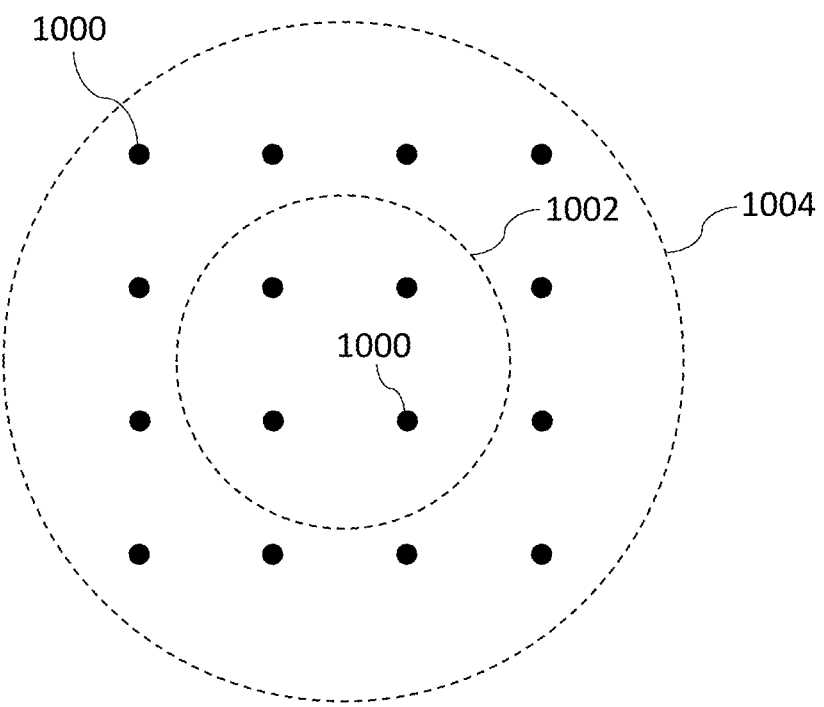
FIG. 10 illustrates schematically the illumination of a plurality of points on a tear film or cornea.
Figure 9:
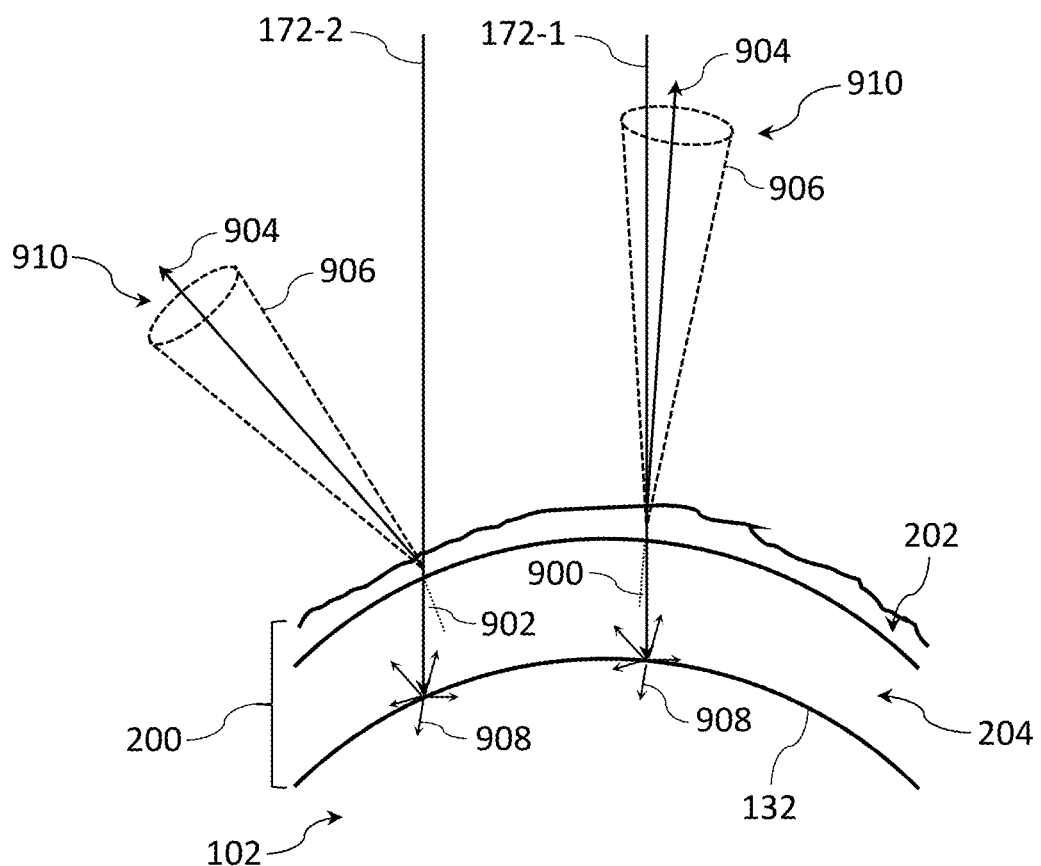
FIG. 9 illustrates schematically a model of specular reflection and scattering consistent with the substantially binary intensity distribution seen in FIG. 7.

In certain embodiments, and with reference to FIGS. 8, 9 and 10, a method for obtaining a measure related to the thickness of a tear film 200 on a cornea 102 is implemented by:
(i) Illuminating the tear film or the anterior surface of the cornea at a plurality of points 1000;
(ii) Capturing, with a capture optical system having a capture angle, return signals comprising hyper-reflective signals 910 from the tear film 200 or scattered light 908 from the anterior surface 132 of the cornea 102 at the plurality of points 1000, wherein a first set 1002 of the plurality of points is illuminated with light 172-1 that impinges on the tear film or the anterior surface of the cornea at an angle of incidence 900 sufficiently close to normal incidence such that the hyper-reflectivity signals 910 are within the capture angle, resulting in a set of higher intensity return signals, and a second set 1004 of the plurality of points is illuminated with light 172-2 that impinges on the tear film or the anterior surface of the cornea at an angle of incidence 902 sufficiently far from normal incidence such that the hyper-reflective signals 910 are not within the capture angle, resulting in a set of lower intensity return signals;
(iii) Processing the higher intensity and lower intensity sets of return signals to obtain optical coherence tomography measurements 804-H, 804-L; and
(iv) Calculating, from selected optical coherence tomography measurements of the higher intensity and lower intensity sets of return signals, a measure 808 related to the thickness of the tear film 200.

The limiting angle of incidence that delineates the first and second sets of points 1002, 1004, i.e. the maximum angle of incidence above which the hyper-reflective signals 910 will not be captured, depends on a number of factors. These include the numerical aperture of the illuminating beamlets 172 and the numerical aperture, or capture angle, of the optical system used to capture return signals from the tear film 200 or cornea 102. A lower numerical aperture in either case results in a smaller limiting angle, or equivalently a smaller high intensity central region 702. Importantly, the limiting angle or size of the central region 702 depends also on the nature of the tear film 200, yielding diagnostic value. The limiting angle of incidence is typically between 4 degrees and 8 degrees, but can be up to 15 degrees for some tear films. Therefore the array of beamlets 172 should be generated and directed onto the sample cornea 102 such that at least some of the beamlets 172-1 have an angle of incidence 900 less than 15 degrees, more preferably 8 degrees and most preferably less than 4 degrees. Additionally, at least some of the beamlets 172-2 should have an angle of incidence 902 greater than 4 degrees, more preferably greater than 8 degrees, and most preferably greater than 15 degrees.

In the above-described embodiment the reflectivity image 700 of FIG. 7 was obtained by illuminating the tear film 200 or cornea 102 at a plurality of points 1000 simultaneously with an array of beamlets 172. While this is preferred for reasons of acquisition speed and minimisation of eye motion artefacts, it is also possible to illuminate the tear film or cornea at a plurality of points sequentially, e.g. using a scanning beam OCT apparatus, with the subsequent analysis of the reflectivity image 700 or return signals proceeding in an equivalent fashion.

Although the invention has been described with reference to specific examples, it will be appreciated by those skilled in the art that the invention may be embodied in many other forms.

What is claimed is:

1. An apparatus for measuring one or more properties of a cornea, said apparatus comprising:
a first optical system comprising an optical source and a spatial sampling element for generating a converging array of discrete, focused beamlets configured to impinge simultaneously on a plurality of points across at least a portion of a front surface of a cornea; and
a second optical system for:
capturing reflected or scattered light from said front surface and reflected or scattered light from a second surface or interface of said cornea;
measuring relative phase between the reflected or scattered light from said front surface and the reflected or scattered light from said second surface or interface across the portion of said cornea illuminated by said beamlets; and
monitoring said relative phase over time to obtain information on one or more properties of said cornea across the illuminated portion.

2. The apparatus according to claim 1, wherein said apparatus is configured such that, in use, the angle of incidence of said beamlets on said front surface is within 3 degrees of normal incidence.

3. The apparatus according to claim 1, wherein said spatial sampling element comprises a lenslet array.

4. The apparatus according to claim 1, wherein the reflected or scattered light from said front surface and from said second surface or interface is captured with said spatial sampling element, or with a second spatial element.

5. The apparatus according to claim 1, wherein said apparatus comprises a processor for:
producing, from the relative phase measurements, a map of relative phase across the illuminated portion of said cornea; and
monitoring said relative phase over time to determine time variations in said map.

6. The apparatus according to claim 5, wherein said apparatus comprises an interferometer for interfering the reflected or scattered light from said front surface and from said second surface or interface with a reference beam, to generate one or more interferograms.

7. The apparatus according to claim 6, wherein said processor is configured to utilise said one or more interferograms to track the location of said beamlets on said front surface, for registering two or more maps of relative phase acquired at different times.

8. The apparatus according to claim 5, wherein said optical source comprises a multi-wavelength optical source, and wherein said processor is configured to calculate, from said map of relative phase, a tomographic profile of said cornea.

9. The apparatus according to claim 8, wherein said tomographic profile comprises one or more of amplitude, phase or optical path length between said front surface and said second surface or interface.

10. The apparatus according to claim 9, wherein said second surface or interface comprises the posterior surface of said cornea, such that said optical path length comprises a measure of corneal thickness.

11. The apparatus according to claim 9, wherein said processor is configured to determine, from time variations in said optical path length, a biomechanical response of said cornea to relative differences between intraocular pressure and an external pressure on said cornea.

12. The apparatus according to claim 11, wherein said processor is configured to determine a biomechanical response of said cornea to periodic intraocular pressure variations associated with the ocular pulse.

13. The apparatus according to claim 11, wherein said apparatus is configured to vary said external pressure on said cornea.

14. The apparatus according to claim 13, wherein said apparatus is configured to vary said external pressure by applying a source of distributed sound waves, or by varying the ambient pressure at said cornea.

15. The apparatus according to claim 9, wherein said processor is configured to:
measure time variations in the thickness of a tear film on said cornea; and
subtract the measured time variations in tear film thickness from said optical path length to provide a normalised measurement of corneal optical path length.

16. The apparatus according to claim 1, wherein said apparatus is configured to measure time variations in the thickness of a tear film on said cornea.

17. A method for measuring one or more properties of a cornea, said method comprising the steps of:
generating a converging array of discrete, focused beamlets configured to impinge simultaneously on a plurality of points across at least a portion of a front surface of a cornea;
capturing reflected or scattered light from said front surface and reflected or scattered light from a second surface or interface of said cornea;
measuring relative phase between the reflected or scattered light from said front surface and the reflected or scattered light from said second surface or interface across the portion of said cornea illuminated by said beamlets; and
monitoring said relative phase over time to obtain information on one or more properties of said cornea across the illuminated portion.

18. The method according to claim 17, further comprising the steps of:
producing, from the relative phase measurements, a map of relative phase across the illuminated portion of said cornea; and
monitoring said relative phase over time to determine time variations in said map.

19. The method according to claim 18, wherein said beamlets are generated from a multi-wavelength optical source, and wherein said map of relative phase provides a tomographic profile of said cornea.

20. The method according to claim 19, wherein said tomographic profile comprises one or more of amplitude, phase or optical path length between said front surface and said second surface or interface.

21. The method according to claim 20, further comprising the step of determining, from time variations in said optical path length, a biomechanical response of said cornea to relative differences between intraocular pressure and an external pressure on said cornea.

22. The method according to claim 21, wherein a biomechanical response of said cornea to periodic intraocular pressure variations associated with the ocular pulse is determined.

23. The method according to claim 17, further comprising the step of measuring time variations in the thickness of a tear film on said cornea.

24. An apparatus for measuring one or more properties of a cornea, said apparatus comprising an optical system for:
generating a converging array of discrete, focused beamlets configured to impinge simultaneously on a plurality of points across at least a portion of a first surface or interface of a cornea;
capturing reflected or scattered light from said first surface or interface and reflected or scattered light from a second surface or interface of said cornea;
measuring relative phase between the first and second surfaces or interfaces across the portion of said cornea illuminated by said beamlets; and
monitoring said relative phase over time to obtain information on one or more properties of said cornea across the illuminated portion.

25. The apparatus according to claim 24, wherein said optical system is configured to measure the phases of said first and second surfaces or interfaces relative to a reference beam, or relative to a reflection from a tear film on said cornea.

26. The apparatus according to claim 24, wherein said apparatus comprises a processor for:
producing, from the relative phase measurements, a map of relative phase across the illuminated portion of said cornea; and
monitoring said relative phase over time to determine time variations in said map.

27. The apparatus according to claim 26, wherein said optical system comprises a multi-wavelength source for generating said beamlets, and wherein said processor is configured to calculate, from said map of relative phase, a tomographic profile of said cornea.

28. A method for measuring one or more properties of a cornea, said method comprising the steps of:
- generating a converging array of discrete, focused beamlets configured to impinge simultaneously on a plurality of points across at least a portion of a first surface or interface of a cornea;
- capturing reflected or scattered light from said first surface or interface and reflected or scattered light from a second surface or interface of said cornea;
- measuring relative phase between said first and second surfaces or interfaces across the portion of said cornea illuminated by said beamlets; and
- monitoring said relative phase over time to obtain information on one or more properties of said cornea across the illuminated portion.

* * * * *